United States Patent
Hong et al.

(10) Patent No.: US 12,226,605 B2
(45) Date of Patent: Feb. 18, 2025

(54) ULTRASOUND MASK AND SKIN CARE DEVICE COMPRISING SAME

(71) Applicant: LG INNOTEK CO., LTD., Seoul (KR)

(72) Inventors: Beom Sun Hong, Seoul (KR); Min Seok Oh, Seoul (KR); Kab Young Kim, Seoul (KR); Sang Young Lee, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 791 days.

(21) Appl. No.: 17/605,300

(22) PCT Filed: Apr. 10, 2020

(86) PCT No.: PCT/KR2020/004885
§ 371 (c)(1),
(2) Date: Oct. 21, 2021

(87) PCT Pub. No.: WO2020/222439
PCT Pub. Date: Nov. 5, 2020

(65) Prior Publication Data
US 2022/0233887 A1    Jul. 28, 2022

(30) Foreign Application Priority Data

Apr. 29, 2019 (KR) .................. 10-2019-0049669
May 17, 2019 (KR) .................. 10-2019-0058195

(51) Int. Cl.
*A61M 37/00*   (2006.01)
*A61H 23/00*   (2006.01)
(Continued)

(52) U.S. Cl.
CPC ......... *A61M 37/0092* (2013.01); *A61H 23/00* (2013.01); *A61H 23/0245* (2013.01);
(Continued)

(58) Field of Classification Search
CPC ...... A61M 2210/0606; A61M 2210/04; A61M 37/00; A61M 37/0092; A61N 2007/0034;
(Continued)

(56) References Cited

U.S. PATENT DOCUMENTS 6,472,798 B2   10/2002  Kishimoto
9,561,357 B2   2/2017   Hall et al.
(Continued)

FOREIGN PATENT DOCUMENTS

| CN | 107041996 | 8/2017 |
| CN | 107126637 | 9/2017 |

(Continued)

OTHER PUBLICATIONS

Korean Office Action dated Feb. 20, 2024 issued in Application No. 10-2019-0058195.
(Continued)

*Primary Examiner* — Gerald Johnson
(74) *Attorney, Agent, or Firm* — KED & ASSOCIATES, LLP

(57) ABSTRACT

An ultrasound mask according to an embodiment comprises a plurality of interconnection wirings comprising first wirings arranged in a first direction and second wirings arranged in a second direction different from the first direction, each of the first and second wirings being disposed between piezoelectric members, wherein the interconnection wirings come in contact with a protective layer.

20 Claims, 23 Drawing Sheets

(51) Int. Cl.
*A61H 23/02* (2006.01)
*A61N 7/00* (2006.01)
*B06B 1/06* (2006.01)

(52) U.S. Cl.
CPC ............... *A61N 7/00* (2013.01); *B06B 1/0622* (2013.01); *A61M 2210/0606* (2013.01); *A61N 2007/0034* (2013.01); *B06B 2201/76* (2013.01)

(58) Field of Classification Search
CPC ............... A61N 7/00; A61N 2007/0004; A61H 23/0245; A61H 23/00; B06B 2201/76; B06B 1/0622
See application file for complete search history.

(56) References Cited

U.S. PATENT DOCUMENTS

| | | | |
|---|---|---|---|
| 2005/0162045 A1 | 7/2005 | Xu et al. | |
| 2008/0139943 A1* | 6/2008 | Deng ................ | A61M 37/0092 600/459 |
| 2014/0276247 A1 | 9/2014 | Hall et al. | |
| 2016/0346529 A1 | 12/2016 | Cazares Delgadillo et al. | |
| 2017/0100585 A1 | 4/2017 | Hall et al. | |
| 2019/0328354 A1* | 10/2019 | Xu ....................... | H10N 30/073 |

FOREIGN PATENT DOCUMENTS

| | | |
|---|---|---|
| CN | 109589507 | 4/2019 |
| CN | 109589508 | 4/2019 |
| KR | 10-2001-0062423 | 7/2001 |
| KR | 10-2006-0066508 | 6/2006 |
| KR | 10-1096600 | 12/2011 |
| KR | 10-2015-0135335 | 12/2015 |
| KR | 10-2016-0035202 | 3/2016 |
| KR | 10-2016-0119093 | 10/2016 |
| KR | 10-2017-0123067 | 11/2017 |

OTHER PUBLICATIONS

International Search Report dated Jul. 29, 2020 issued in Application No. PCT/KR2020/004885.
Chinese Office Action dated May 17, 2023 issued in Application No. 202080032154.2.

* cited by examiner

[FIG. 1]
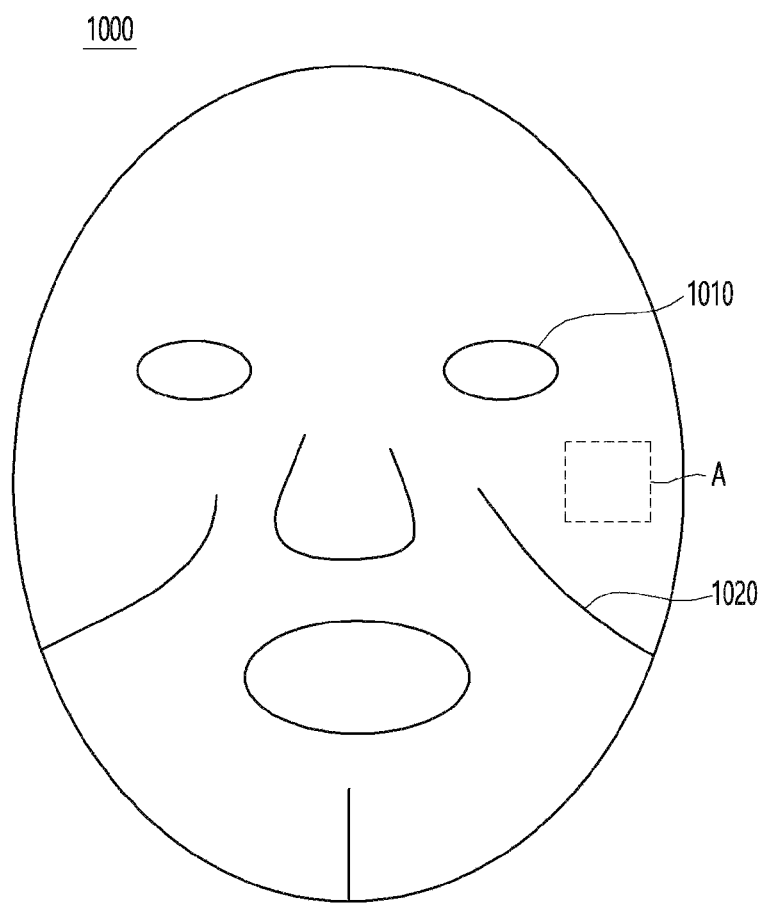

[FIG. 2]
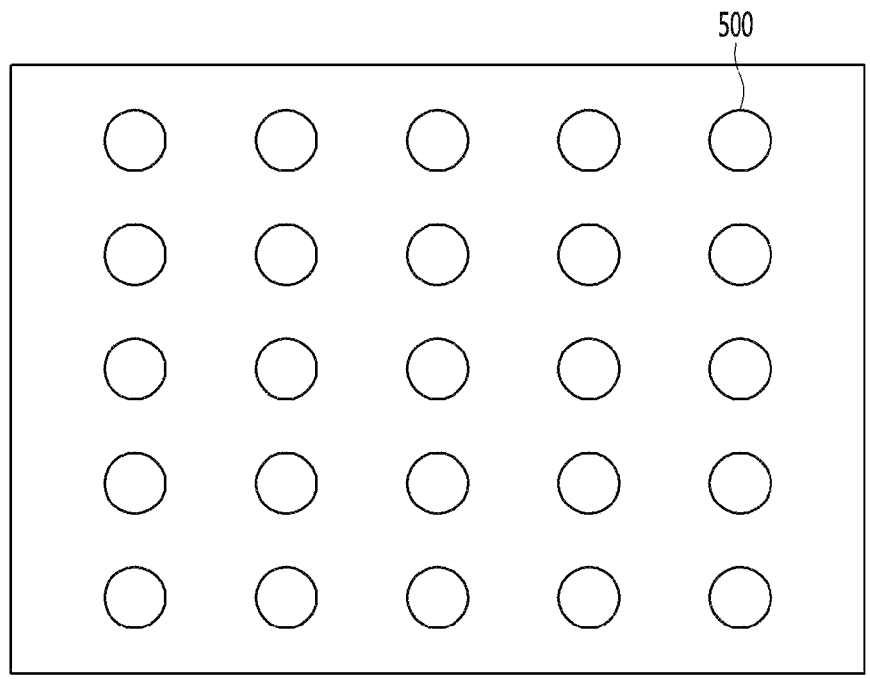
[FIG. 3]
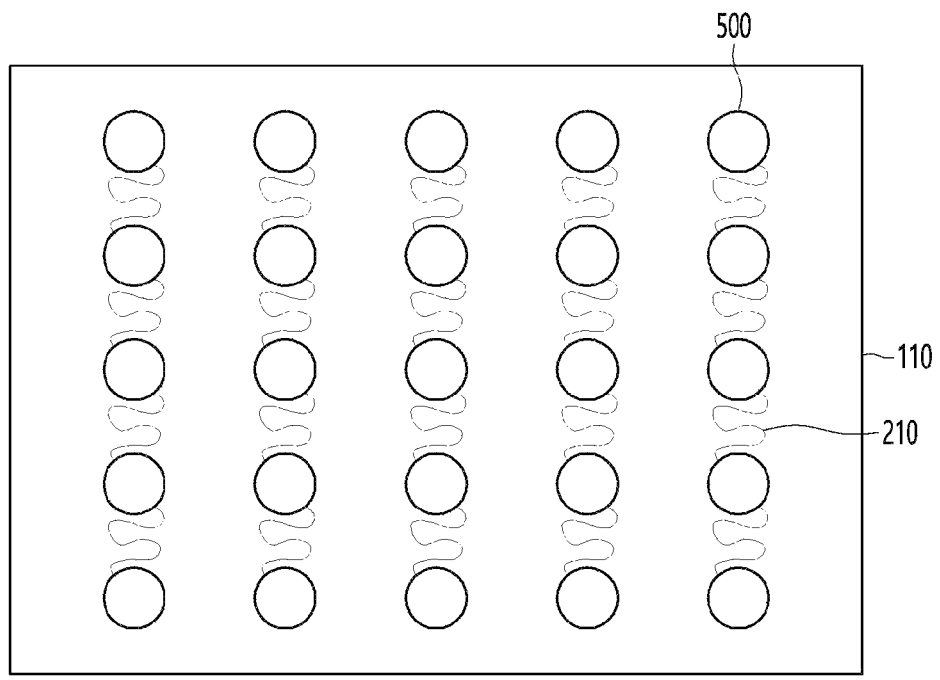

[FIG. 4]
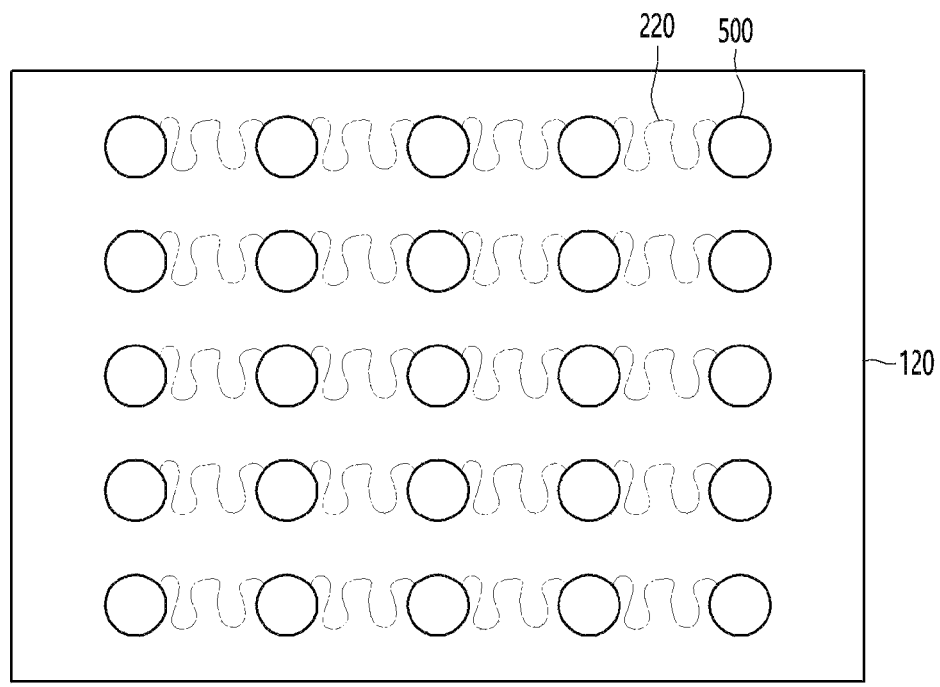
[FIG. 5]
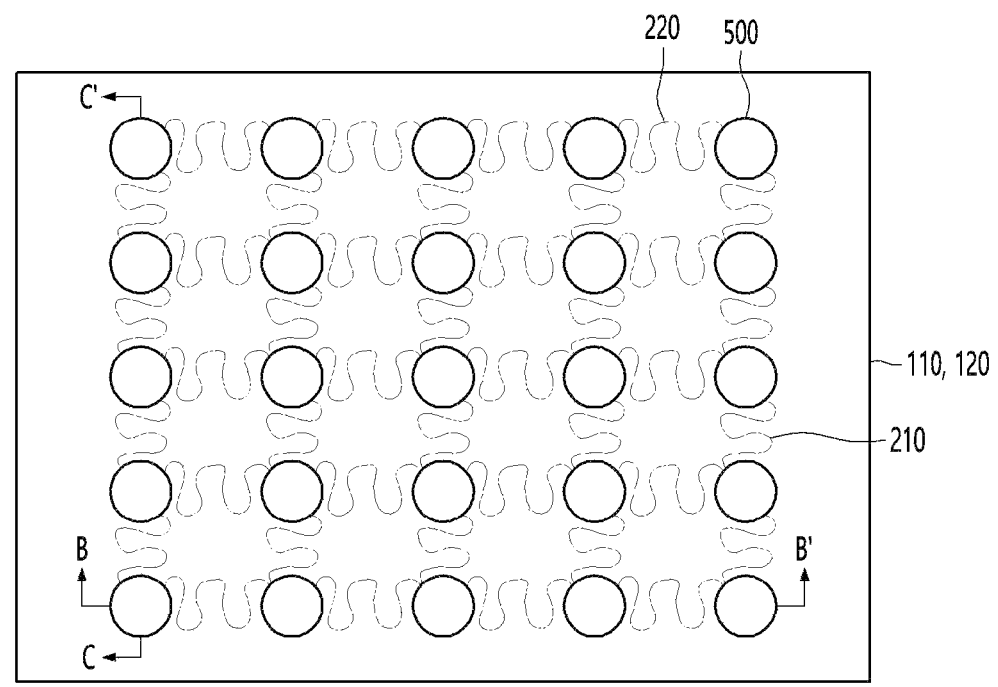

[FIG. 6]
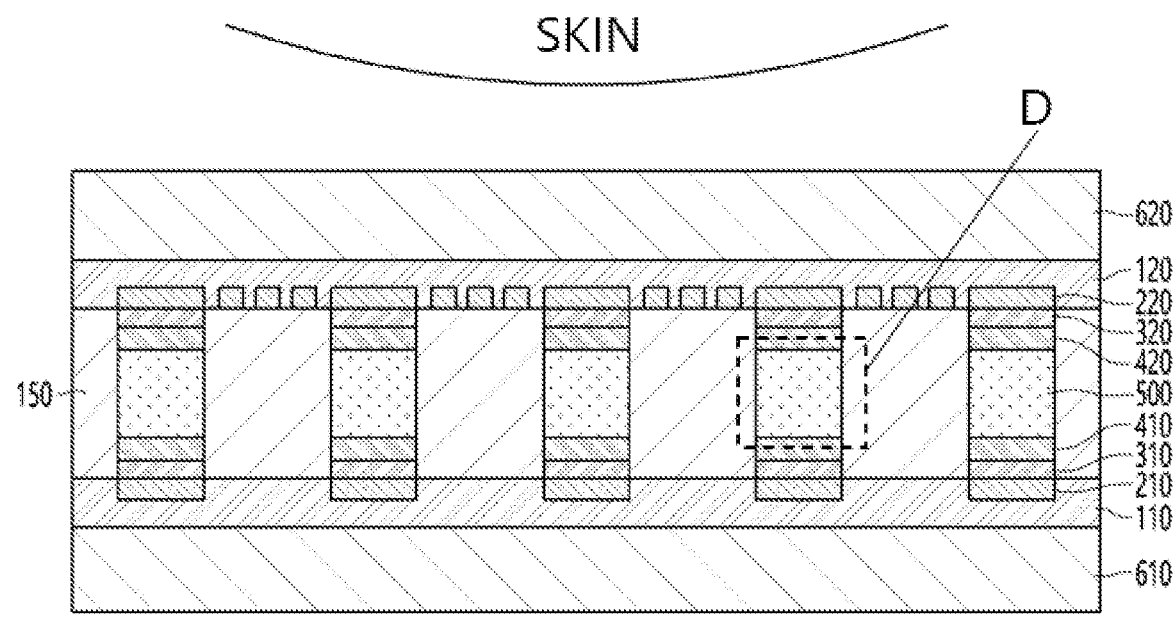
[FIG. 7]
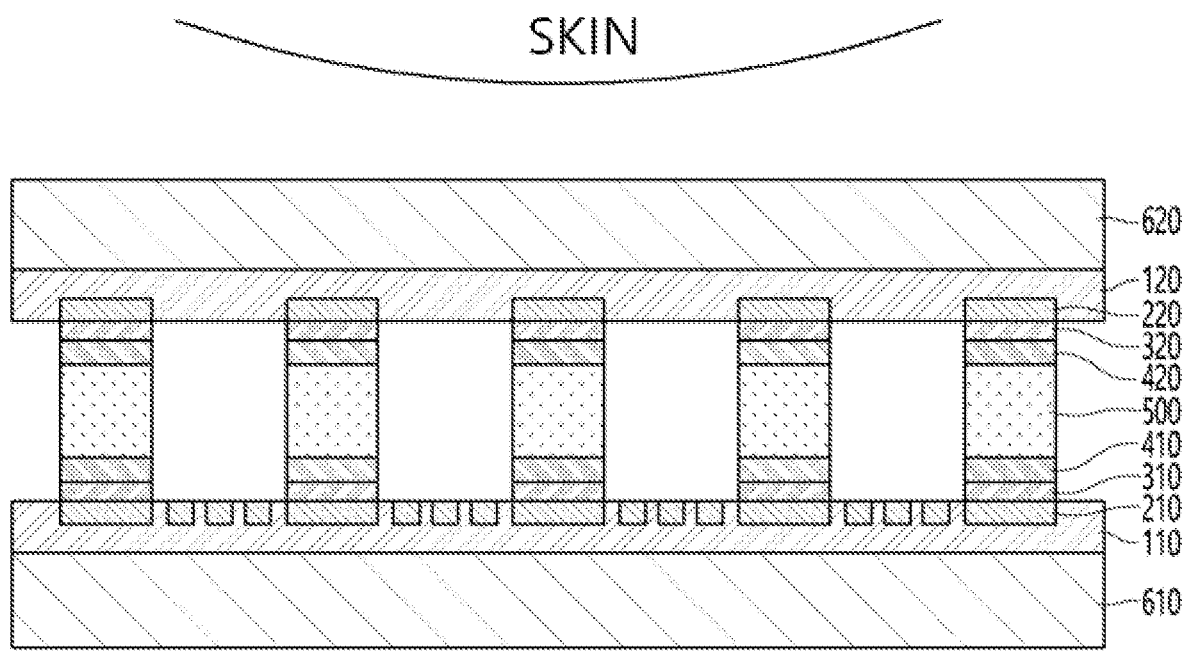

【FIG. 8】
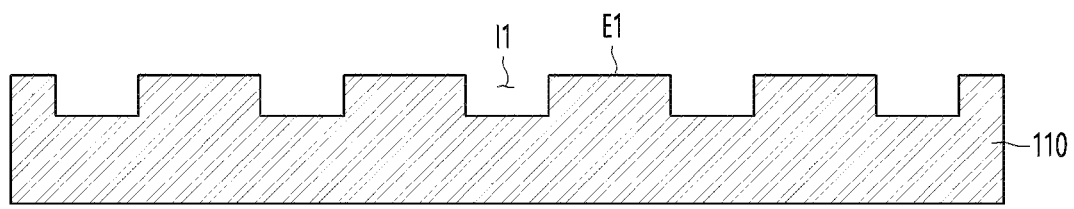
【FIG. 9】
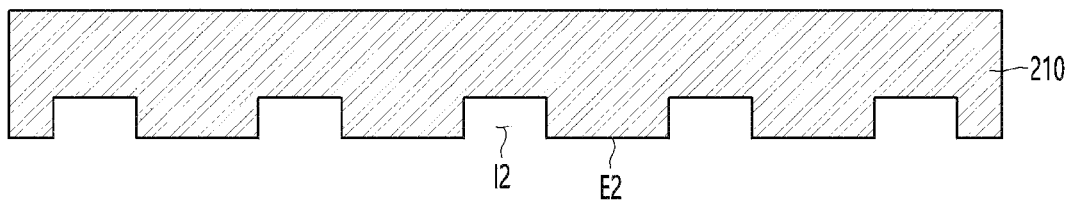
【FIG. 10】
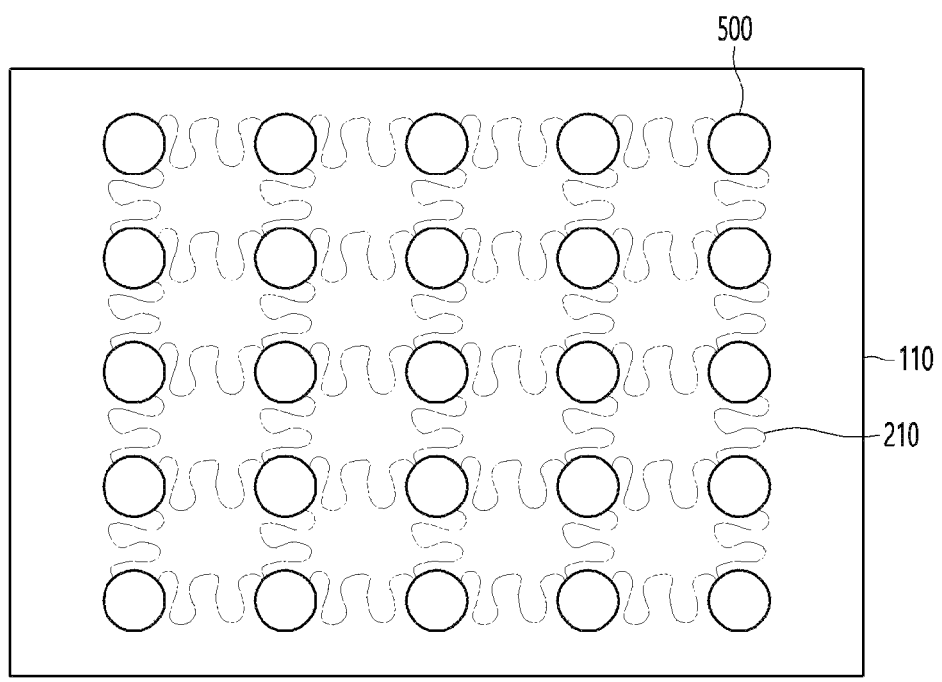

[FIG. 11]
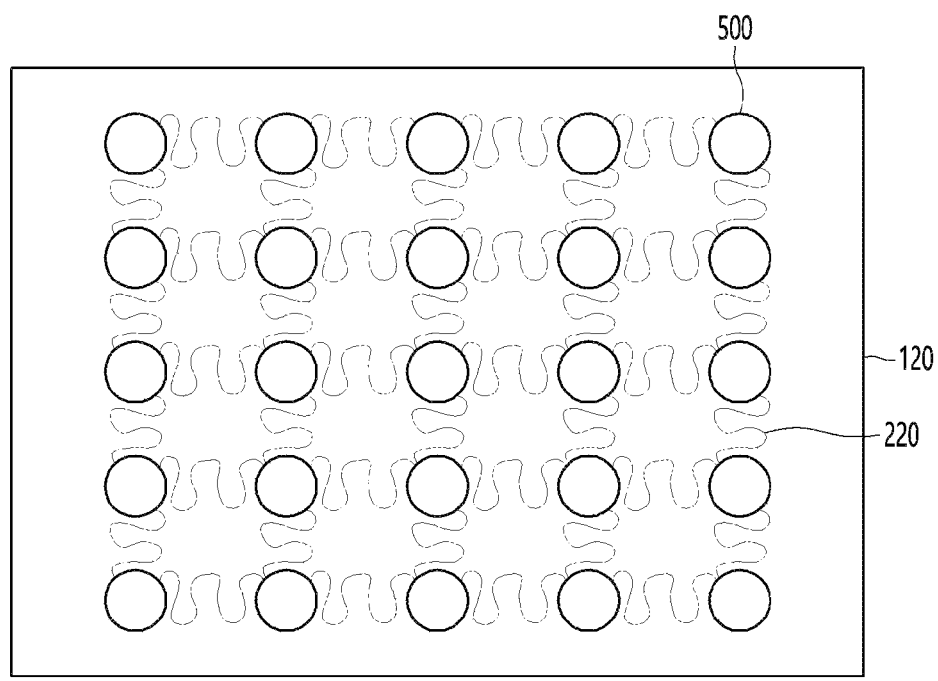
[FIG. 12]
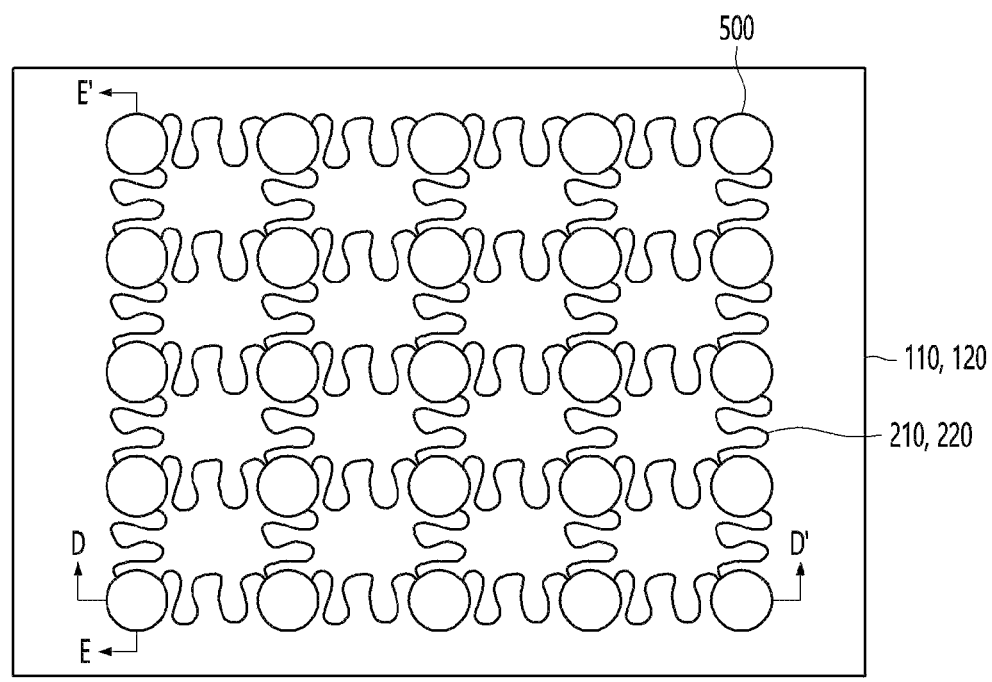

【FIG. 13】
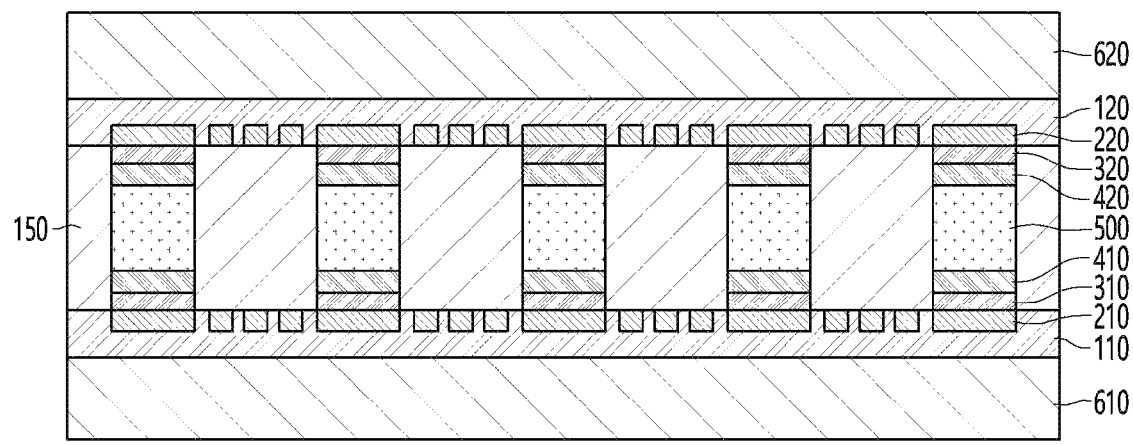
【FIG. 14】
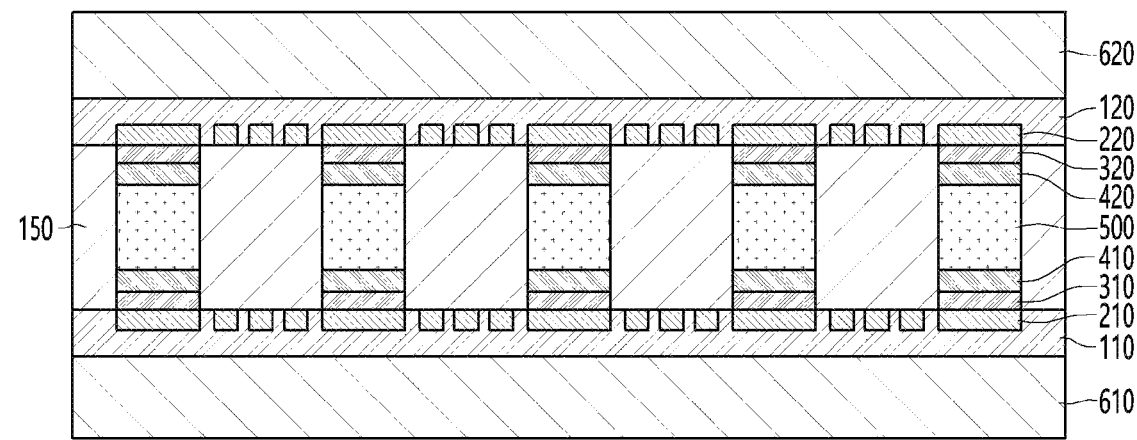

【FIG. 15】
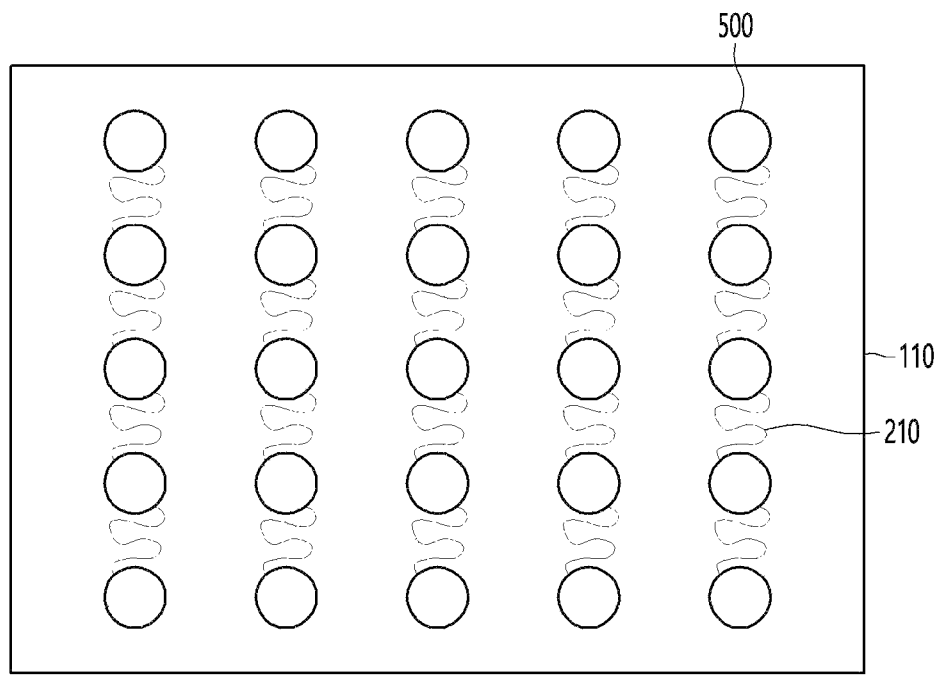
【FIG. 16】
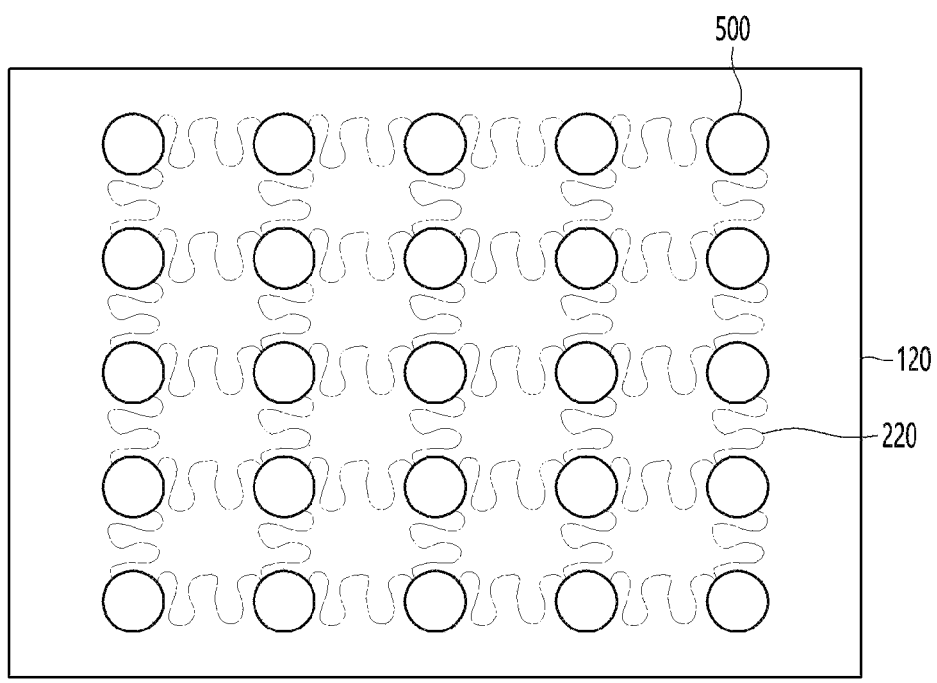

[FIG. 17]
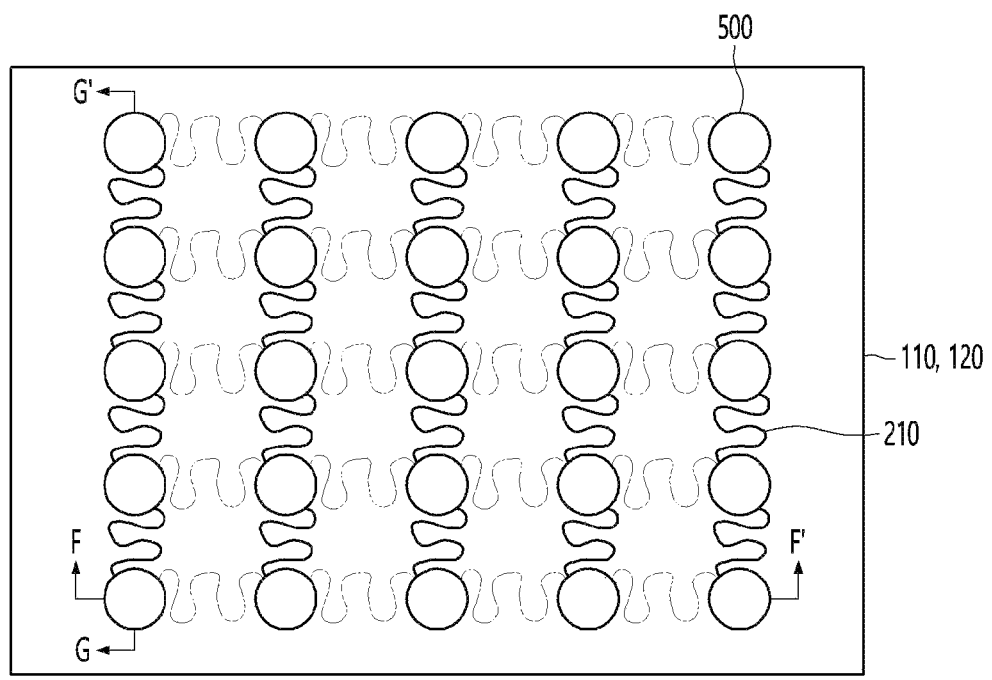
[FIG. 18]
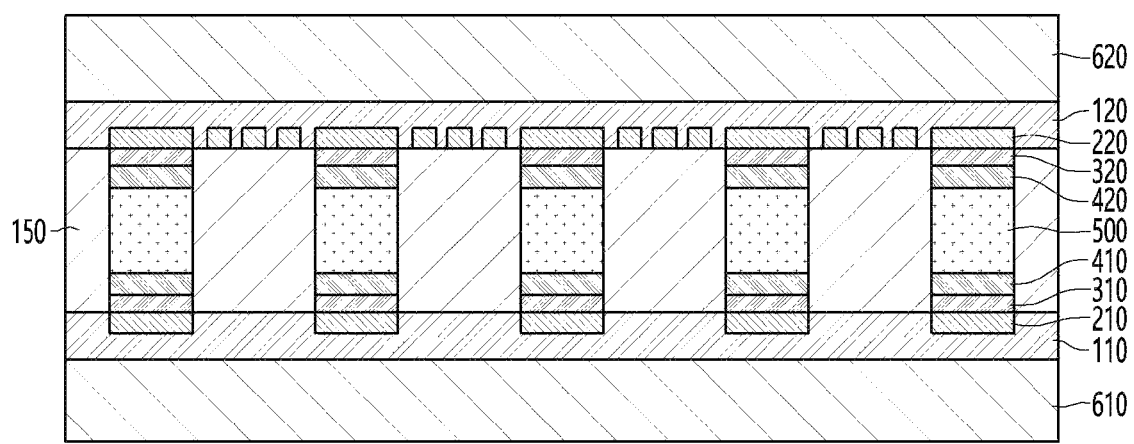

[FIG. 19]
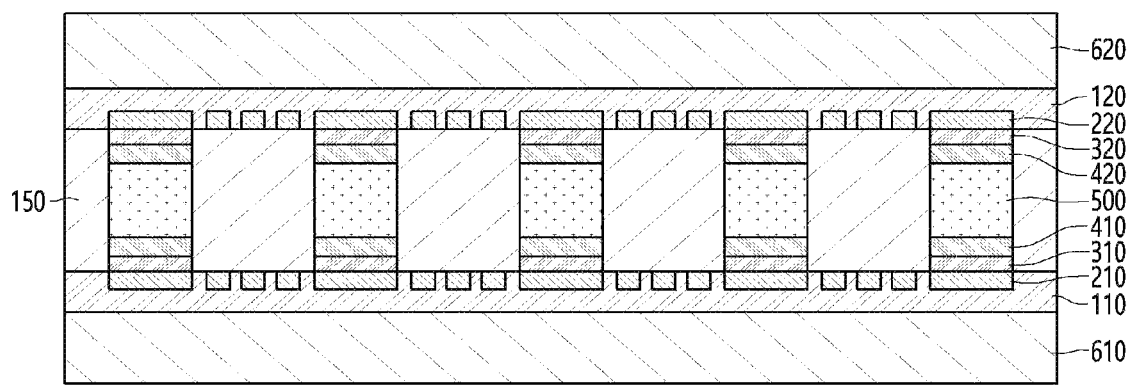
[FIG. 20]
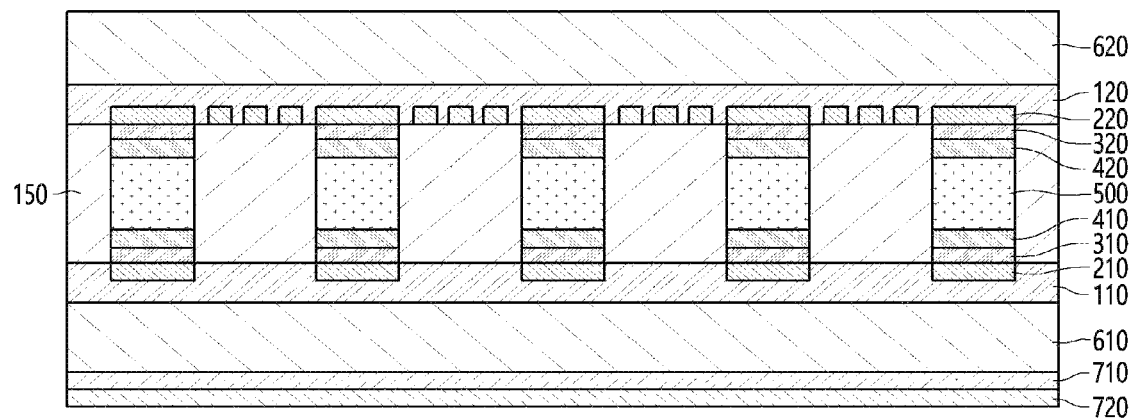

[FIG. 21]
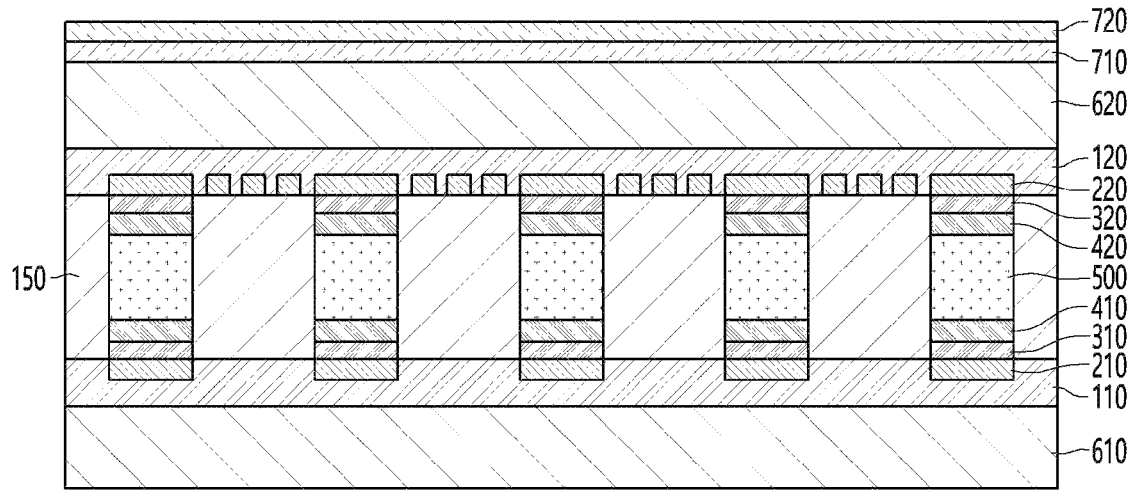
[FIG. 22]
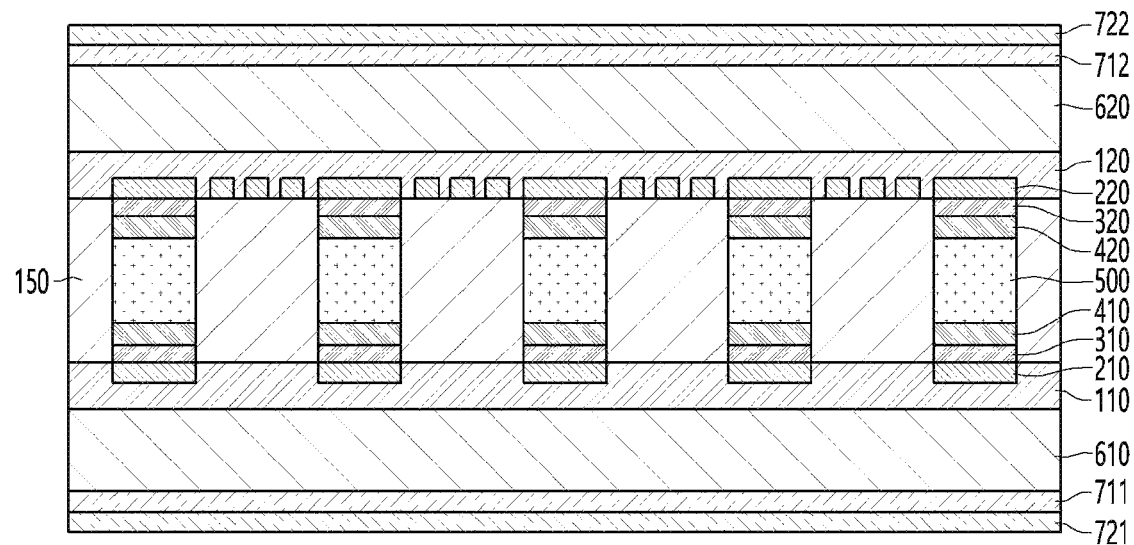

【FIG. 23】
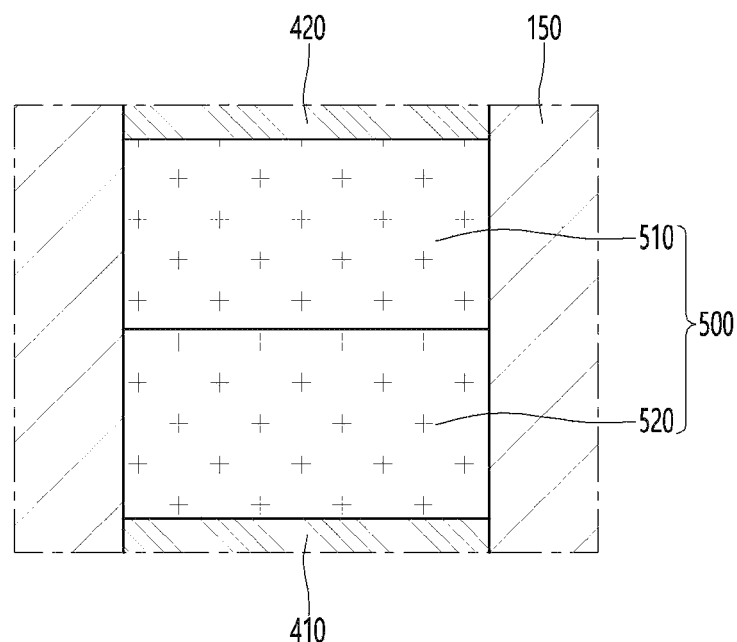
【FIG. 24】
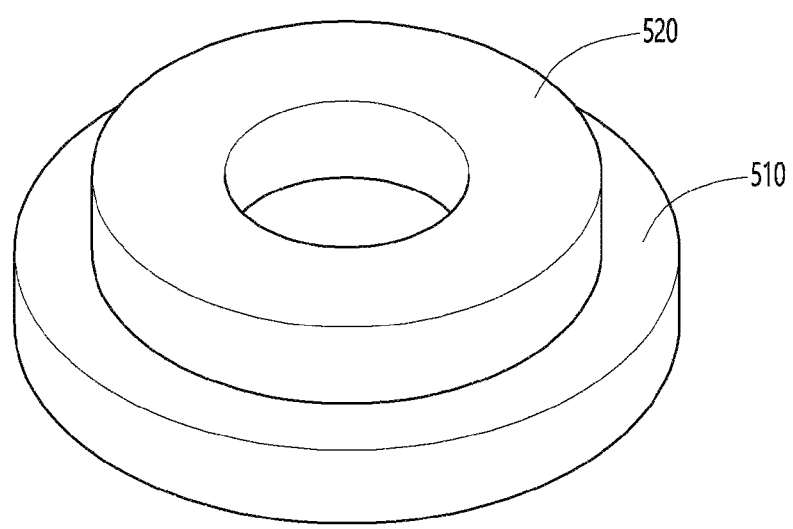

【FIG. 25】
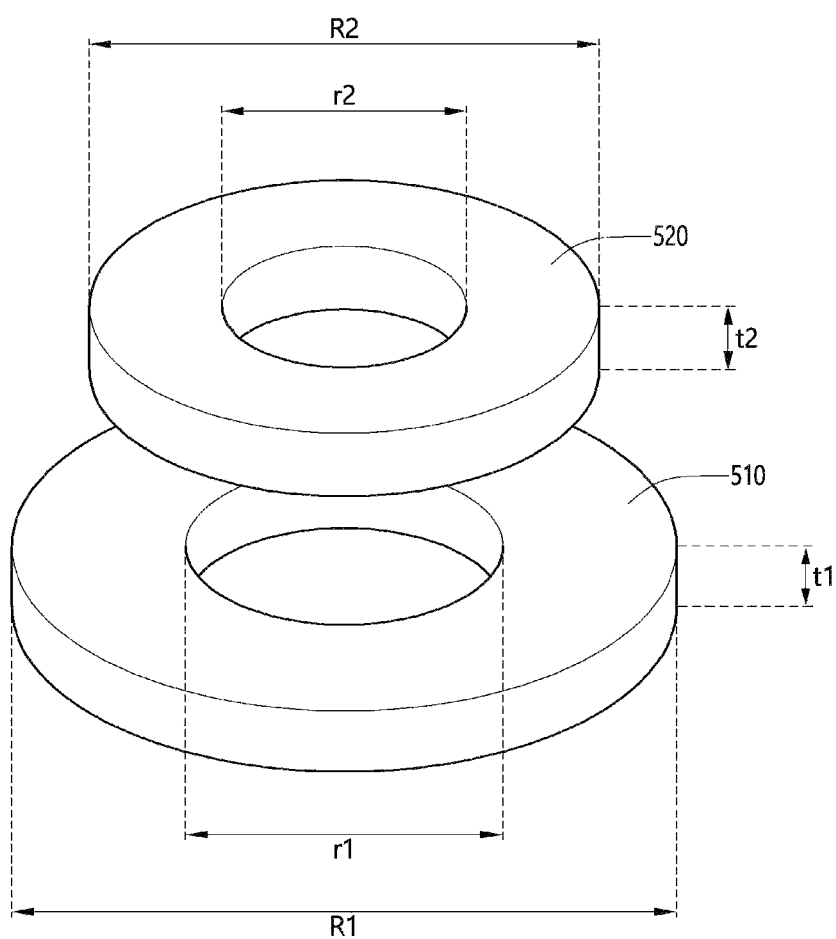

[FIG. 26A]
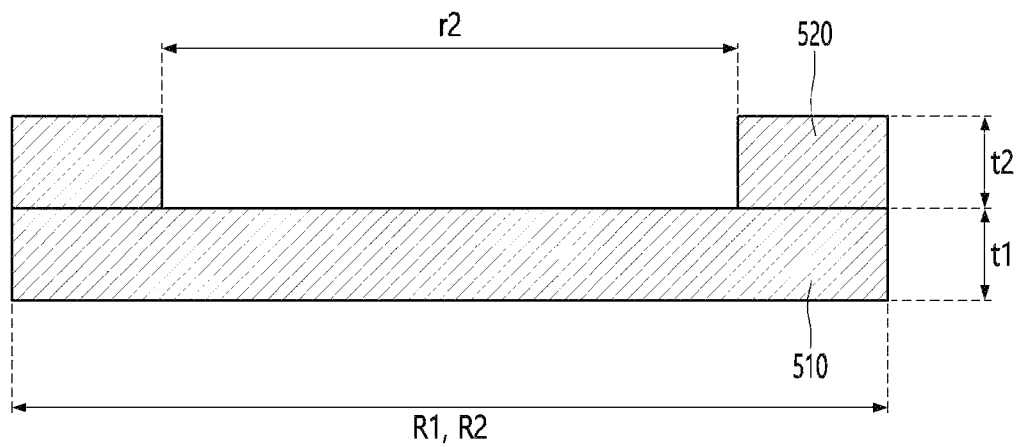
[FIG. 26B]
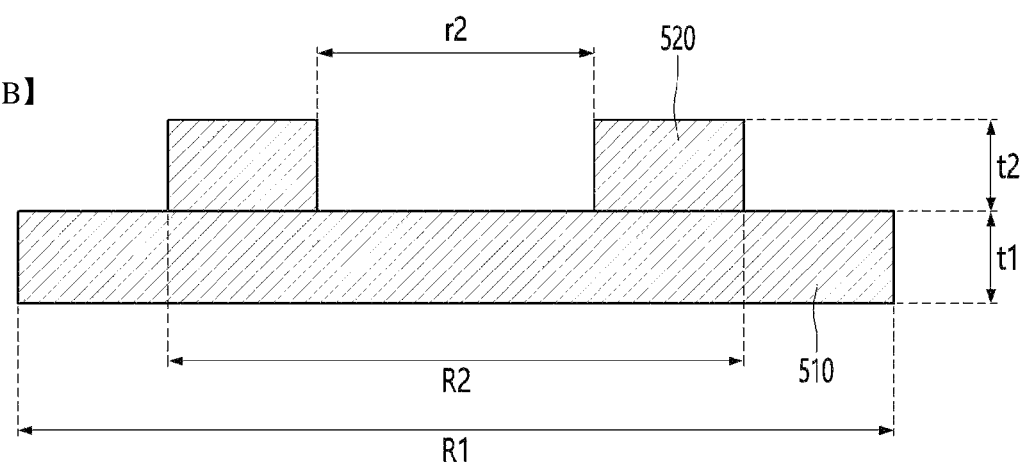
[FIG. 26C]
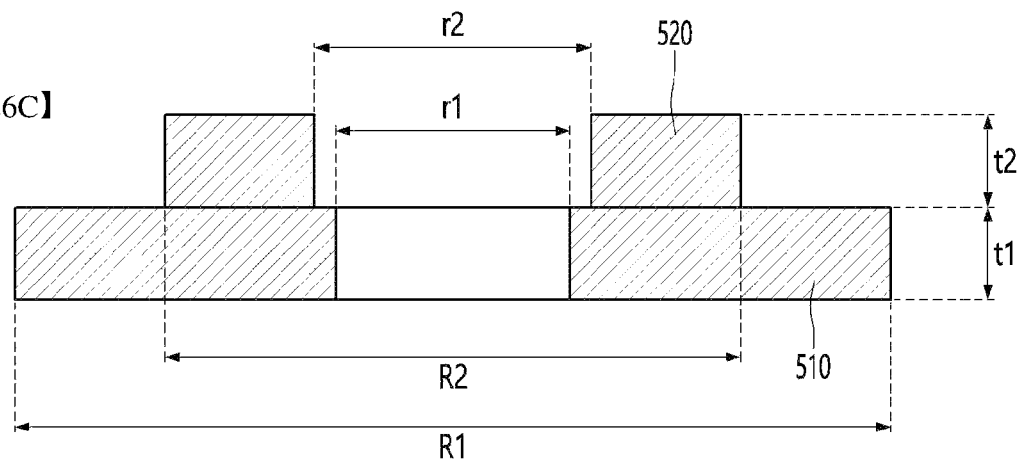

[FIG. 27A]
[FIG. 27B]
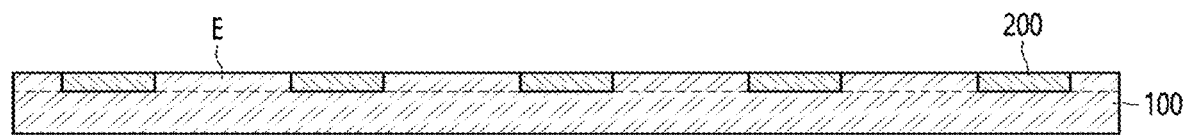
[FIG. 28]
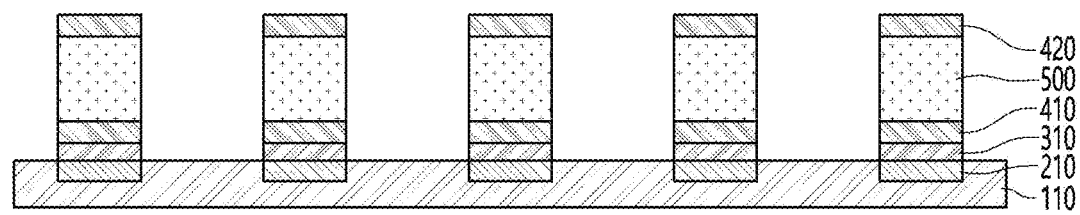
[FIG. 29]
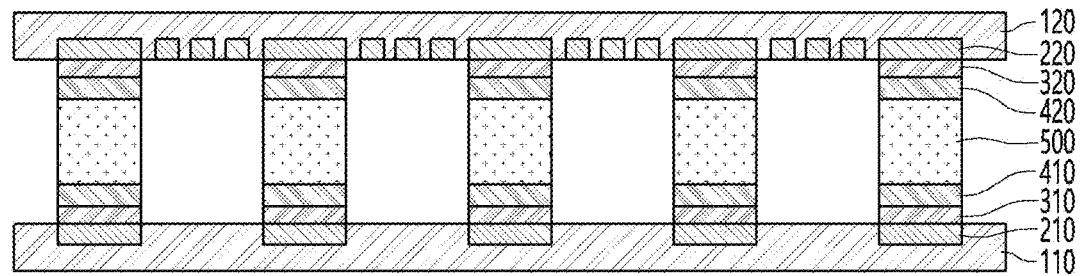

[FIG. 30]
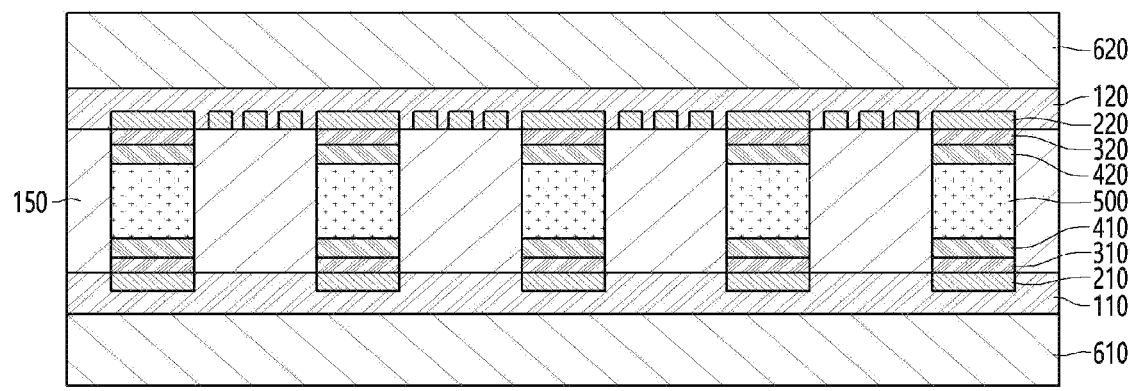
[FIG. 31A]
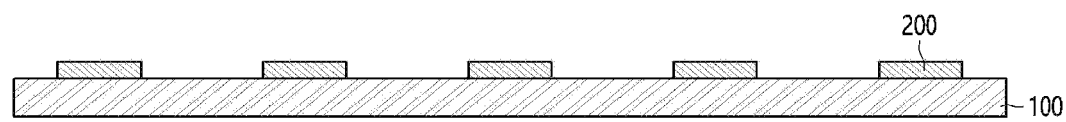
[FIG. 31B]
[FIG. 32]
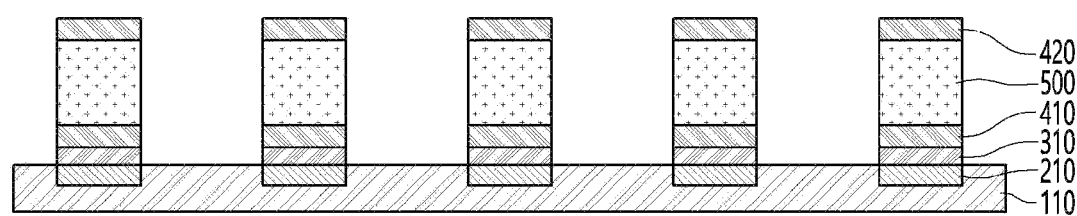

【FIG. 33】
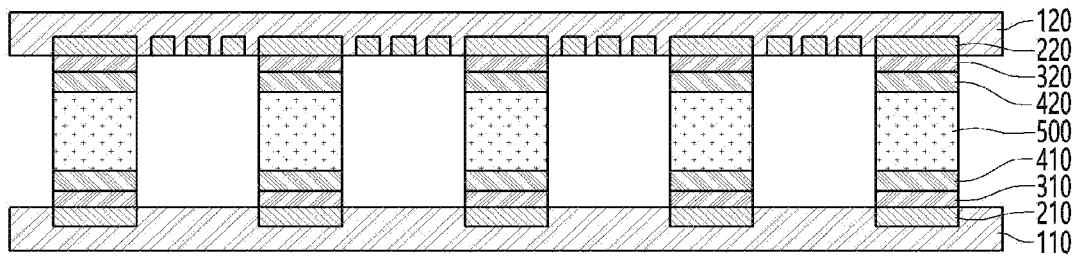
【FIG. 34】
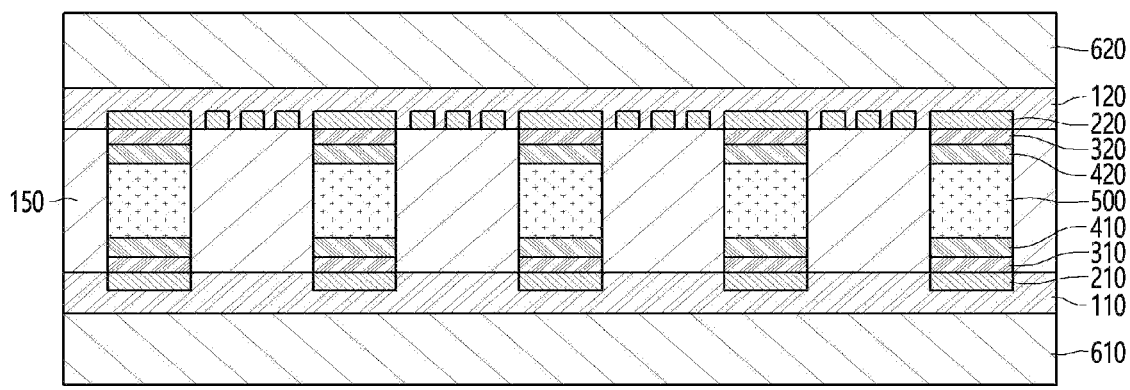
【FIG. 35】
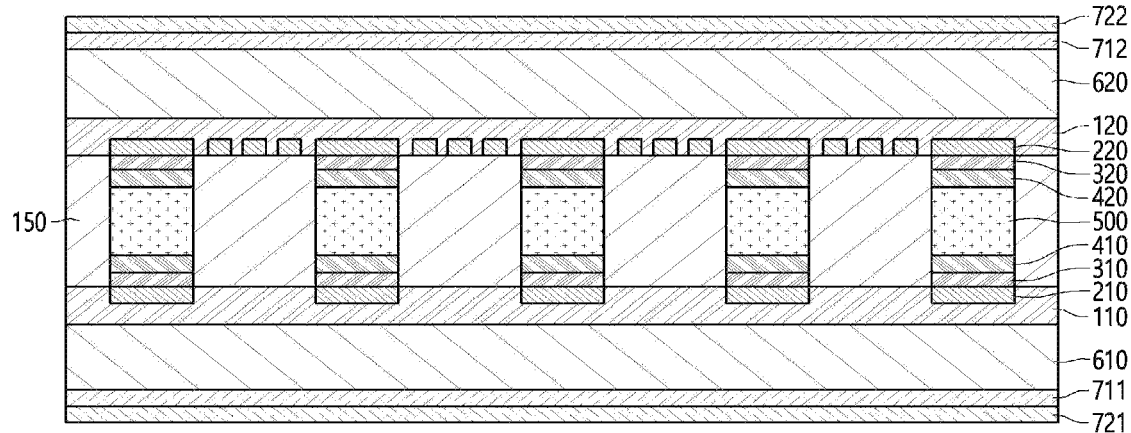

[FIG. 36]
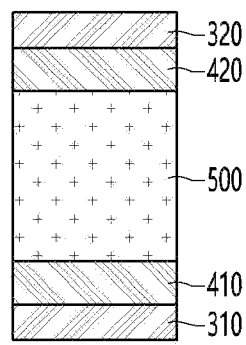
[FIG. 37]
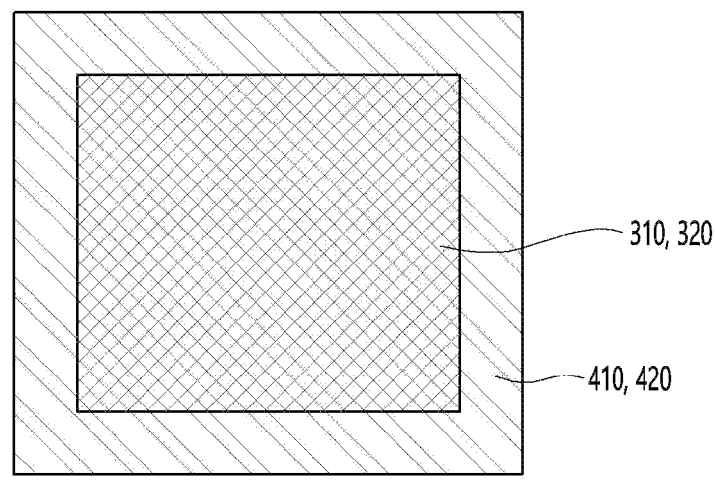

[FIG. 38]
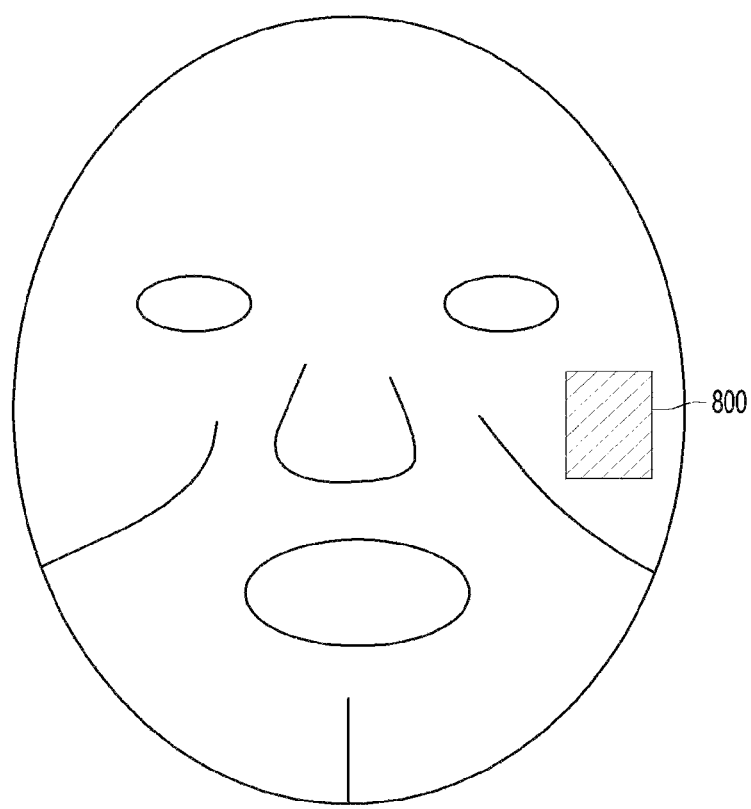

【FIG. 39】
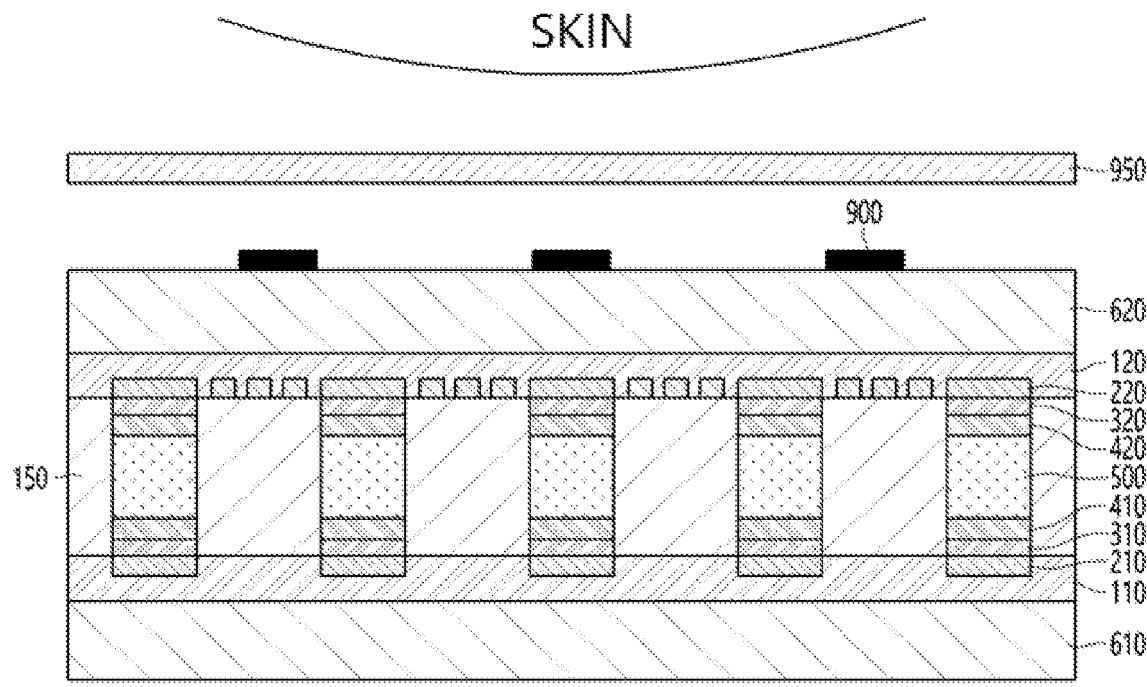
【FIG. 40】
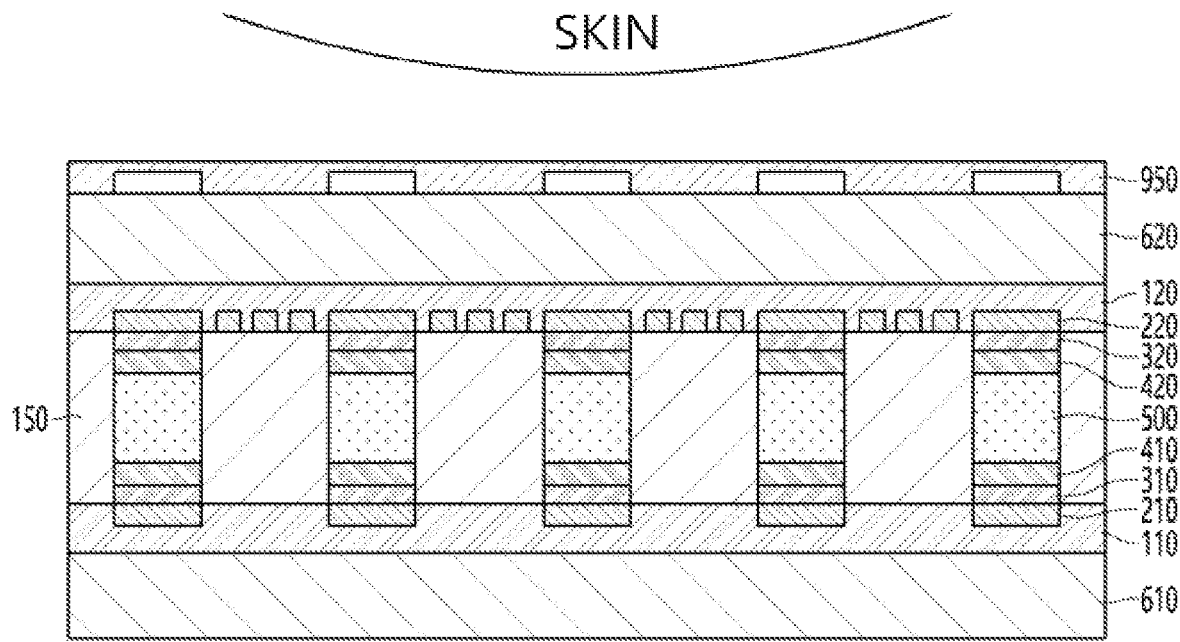

【FIG. 41】
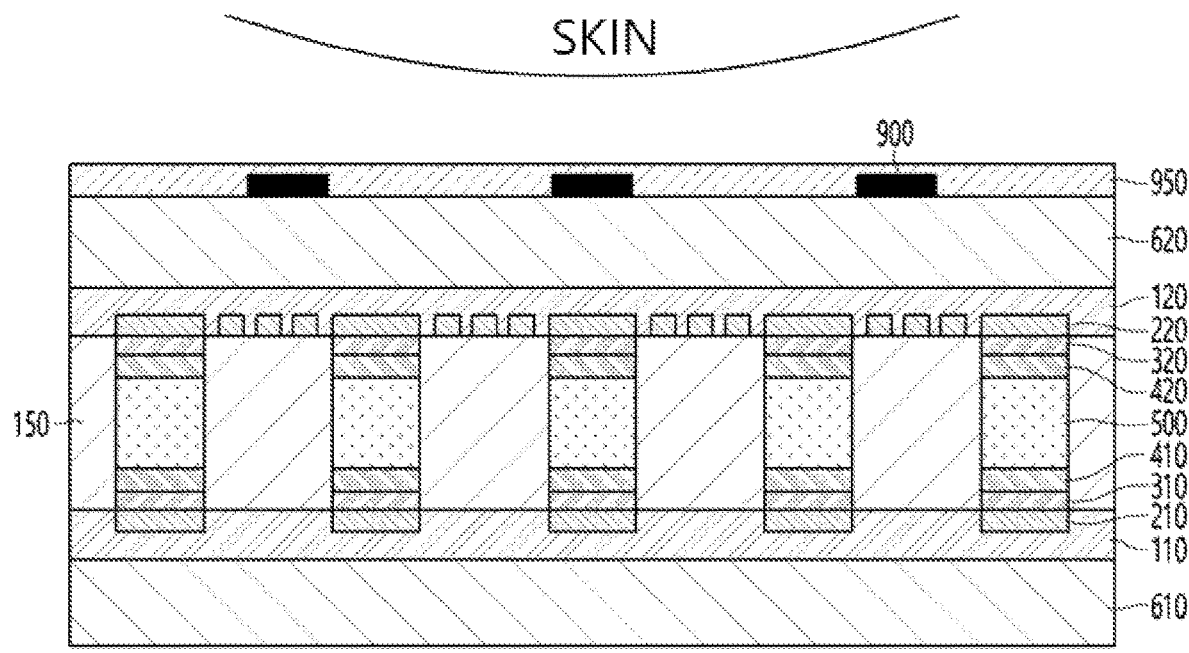
【FIG. 42】
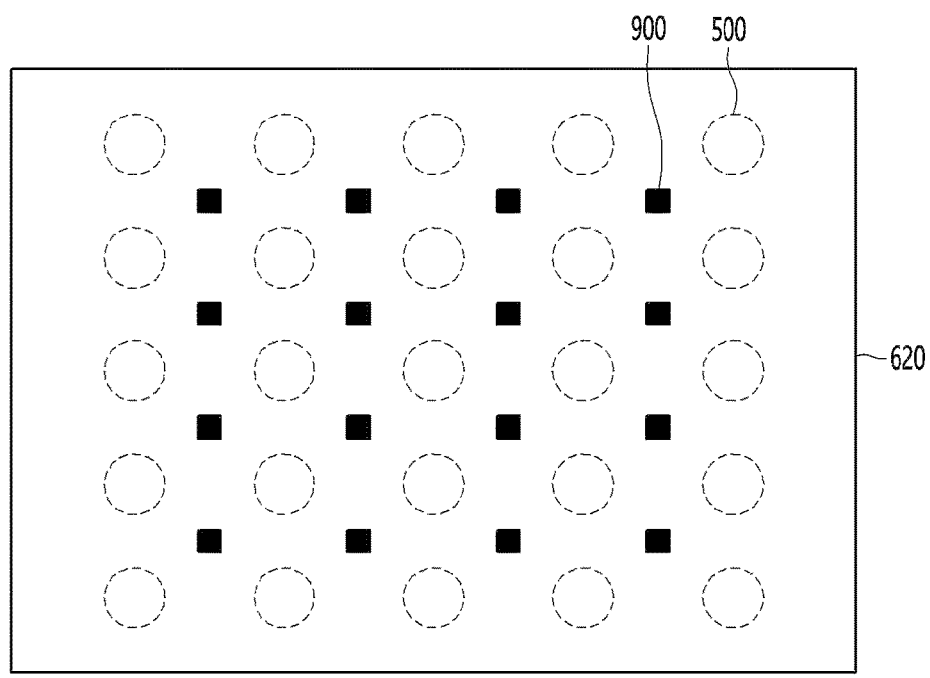

【FIG. 43】
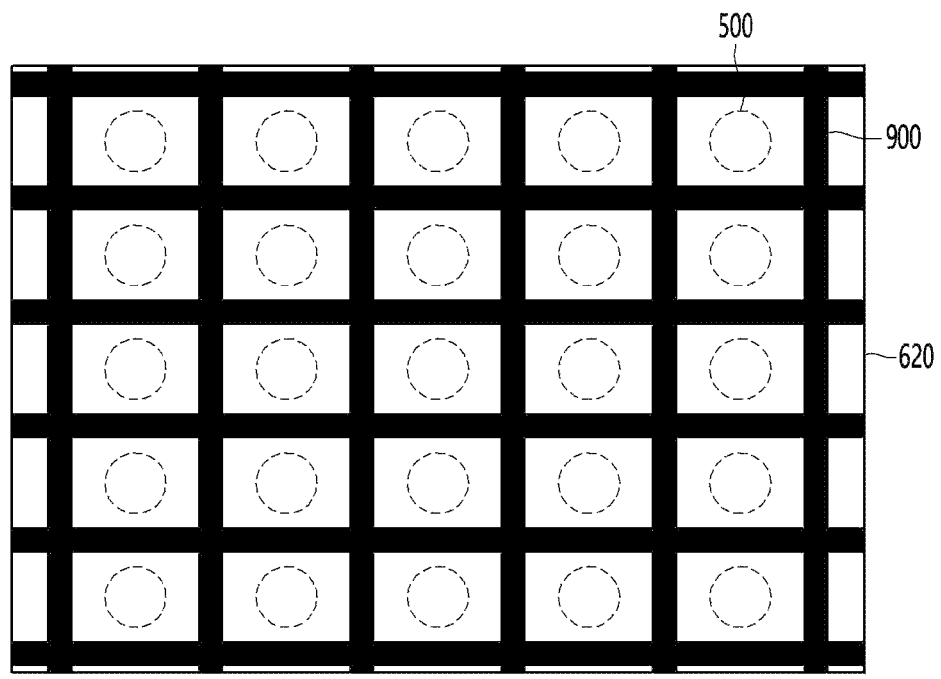
【FIG. 44】
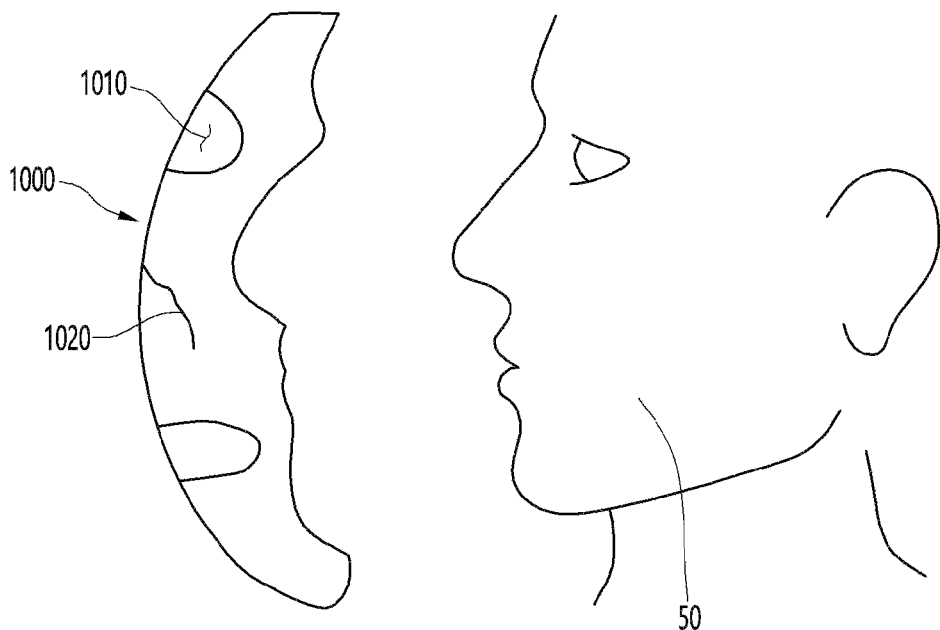

【FIG. 45】
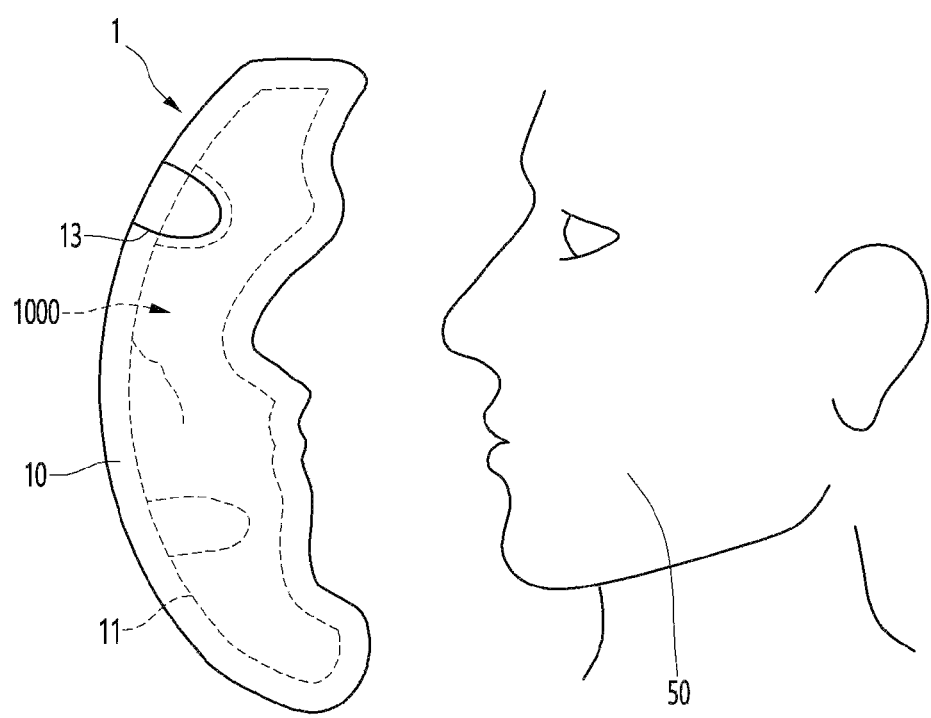

ULTRASOUND MASK AND SKIN CARE DEVICE COMPRISING SAME

CROSS-REFERENCE TO RELATED PATENT APPLICATIONS

This application is a U.S. National Stage Application under 35 U.S.C. § 371 of PCT Application No. PCT/KR2020/004885, filed Apr. 10, 2020, which claims priority to Korean Patent Application Nos. 10-2019-0049669, filed Apr. 29, 2019 and 10-2019-0058195, filed May 17, 2019, whose entire disclosures are hereby incorporated by reference.

TECHNICAL FIELD

An embodiment relates to an ultrasound mask that promotes beauty using an ultrasonic wave having a mid-frequency or low-frequency band of 1 MHz or less.

The embodiment relates to an ultrasound mask that may form a plurality of resonances in the vicinity of a specific frequency and promotes beauty using ultrasonic waves.

BACKGROUND ART

Human skin may be damaged or contaminated depending on external factors such as environmental pollution, ultraviolet rays, stress, and the like, and wrinkles may occur due to internal factors such as aging, hormonal changes, and the like. Recently, as interest in the skin has increased, various devices for skin treatment, beauty, and anti-aging have been developed.

In detail, a device has been developed, which is capable of applying thermal energy to the skin, for example, a device capable of improving skin elasticity by applying infrared energy. In addition, a device using sound waves or light rays has been developed in order to effectively inject cosmetics or drugs into the skin. For example, a device has been developed, which is capable of forming a path through which cosmetics or drugs are injected into the skin using sonophoresis and laserporation. In addition, a device using electric propulsion force has been developed in order to effectively inject cosmetics or drugs into the skin. For example, a device has been developed, which is capable of effectively injecting ionic substances contained in cosmetics or drugs into the skin using iontophoresis, electroporation, and electroosmosis. That is, various devices have been developed, which is capable of caring or treating a user's skin by providing light energy, microcurrent, vibration, or the like to the skin.

In general, the above-described devices may be provided in a form of a patch detachable to the skin, and the devices are attached to a specific skin region to care or treat the skin of the attached region. In addition, the above-described devices are provided in a form of a mask pack disposed to cover the entire user's face to care or treat the facial skin.

However, the devices have a problem that it is difficult to effectively adhere to curved skin surfaces such as both cheeks, nose, and the like. In detail, it may be difficult to effectively adhere to the user's skin due to materials and variable characteristics of the device. Accordingly, the device may be operated in a state in which the device is not completely adhered to the user's skin, and the device may be separated from the user's skin due to the user's movement or vibration of the device during the operation thereof.

In this case, there is a problem that it is difficult for the user to check whether the device is adhered to the skin, and thus, it is difficult to effectively obtain a care effect through the device.

In addition, since the device is applied to a region having various shapes such as a human's face, stretch and restoration characteristics are required, and there is a problem that an internal wiring or the like is damaged due to the characteristics.

Therefore, a new mask capable of solving the above-described problem is required.

DISCLOSURE

Technical Problem

An embodiment is to provide an ultrasound mask capable of easily delivering a substance used for cosmetics or medical purposes to the skin of the human body and having improved reliability.

An embodiment is to provide a piezoelectric member capable of forming a plurality of resonances in a flexion mode and an ultrasound mask including the same.

Technical Solution

An ultrasound mask according to an embodiment includes: a first substrate; a first wiring disposed on an upper surface of the first substrate; a second substrate disposed above the first substrate; a second wiring disposed on a lower surface of the second substrate; a piezoelectric member between the first substrate and the second substrate; a first electrode connected to the first wiring and disposed on a lower surface of the piezoelectric member; and a second electrode connected to the second wiring and disposed on an upper surface of the piezoelectric member, wherein the first wiring and the second wiring have a curvature (mm) of 5R to 15R, and the piezoelectric member generates an ultrasonic wave having a frequency band of 20 kHz to 1 MHz.

Advantageous Effects

The ultrasound mask according to the embodiment can easily transfer a material into the skin of the human body using ultrasonic waves.

In detail, cosmetic substances such as cosmetics can be easily delivered according to a position, shape, and size of an object to be worn by a user through a rigid piezoelectric member, a flexible substrate, and a wiring.

In addition, when the user wears the ultrasound mask through the substrate and the wiring that can be stretched and restored, it is possible to prevent an electrode from being damaged due to deformation of the ultrasound mask.

In addition, it is possible to minimize the loss of ultrasonic waves generated during transmission by controlling the directionality of the ultrasonic waves generated from the piezoelectric member by the matching layer and the backing layer.

In addition, it is possible to minimize the loss of ultrasonic waves generated during transmission by controlling thicknesses of the matching layer and the backing layer and controlling the movement of ultrasonic waves according to the frequency band of the ultrasonic waves generated from the piezoelectric member.

In addition, when the ultrasound mask is stretched or restored, the first wiring and the second wiring having a shape of continuous curvature patterns are stretched or restored together like a spring, and thus a stress effect due to stretch or restoration can be minimized.

In addition, since the first wiring extends only in a first direction and the second wiring extends only in a second direction, it is possible to minimize the constraints depending on the direction when the ultrasound mask according to the first embodiment is stretched or restored. That is, it is possible to improve the flexibility of the ultrasound mask.

In addition, the ultrasound mask according to the embodiment can easily transfer a material into the skin of the human body using ultrasonic waves.

In detail, since the piezoelectric member of the ultrasound mask according to the embodiment can emit ultrasonic waves in a thickness direction by oscillating ultrasonic waves in a flexion mode, the piezoelectric member can oscillate the ultrasonic waves in a wide region of the skin.

In addition, since the piezoelectric member of the ultrasound mask according to the embodiment can radiate the ultrasonic waves in the flexion mode in at least three frequency bands, the ultrasound mask can be used with ultrasonic waves in an appropriate frequency band according to the user's skin condition, and accordingly, it is possible to prevent a decrease in transmission efficiency of ultrasonic waves depending on the user's skin condition.

DESCRIPTION OF DRAWINGS

FIG. 1 is a view illustrating a top surface of an ultrasound mask according to an embodiment.

FIG. 2 is a view illustrating an enlarged top view of region A in FIG. 1.

FIG. 3 is a view illustrating a top view of a first substrate of an ultrasound mask according to a first embodiment.

FIG. 4 is a view illustrating a top view of a second substrate of the ultrasound mask according to the first embodiment.

FIG. 5 is a view illustrating a top view in which the first substrate and the second substrate of the ultrasound mask according to the first embodiment overlap.

FIG. 6 is a view illustrating a cross-sectional view taken along line B-B' in FIG. 5 of the ultrasound mask according to the first embodiment.

FIG. 7 is a view illustrating a cross-sectional view taken along line C-C' in FIG. 5 of the ultrasound mask according to the first embodiment.

FIGS. 8 and 9 are views illustrating cross-sectional views of the first substrate and the second substrate of the ultrasound mask according to the first embodiment.

FIG. 10 is a view illustrating another top view of a first substrate of an ultrasound mask according to a second embodiment.

FIG. 11 is a view illustrating another top view of a second substrate of the ultrasound mask according to the second embodiment.

FIG. 12 is a view illustrating a top view in which the first substrate and the second substrate of the ultrasound mask according to the second embodiment overlap.

FIG. 13 is a view illustrating a cross-sectional view taken along line D-D' in FIG. 12 of the ultrasound mask according to the second embodiment.

FIG. 14 is a view illustrating a cross-sectional view taken along line E-E' in FIG. 12 of the ultrasound mask according to the second embodiment.

FIG. 15 is a view illustrating another top view of a first substrate of an ultrasound mask according to a third embodiment.

FIG. 16 is a view illustrating another top view of a second substrate of the ultrasound mask according to the third embodiment.

FIG. 17 is a view illustrating a top view in which the first substrate and the second substrate of the ultrasound mask according to the third embodiment overlap.

FIG. 18 is a view illustrating a cross-sectional view taken along line F-F' in FIG. 17 of the ultrasound mask according to the third embodiment.

FIG. 19 is a view illustrating a cross-sectional view t taken along line G-G' in FIG. 17 of the ultrasound mask according to the third embodiment.

FIG. 20 is a view illustrating a cross-sectional view taken along line B-B' in FIG. 5 of an ultrasound mask according to a fourth embodiment.

FIG. 21 is a view illustrating a cross-sectional view taken along line B-B' in FIG. 5 of an ultrasound mask according to a fifth embodiment.

FIG. 22 is a view illustrating a cross-sectional view taken along line B-B' in FIG. 5 of an ultrasound mask according to a sixth embodiment.

FIG. 23 is a view illustrating an enlarged view of region D in FIG. 6.

FIG. 24 is a view illustrating a perspective view of a piezoelectric member according to an embodiment.

FIG. 25 is an exploded perspective view of the piezoelectric member according to the embodiment.

FIGS. 26A to 26C are cross-sectional views of FIG. 24 and a view illustrating various shapes of the piezoelectric member.

FIGS. 27A to 30 are views for describing a manufacturing process of the ultrasound mask according to the first to third embodiments.

FIGS. 31A to 35 are views for describing a manufacturing process of the ultrasound mask according to the fourth to sixth embodiments.

FIGS. 36 and 37 are views for describing an overlapping relationship between an adhesive layer and an electrode of the ultrasound mask according to the embodiment.

FIG. 38 is a view illustrating another top surface of the ultrasound mask according to the embodiment.

FIG. 39 is a view illustrating another cross-sectional view taken along line B-B' in FIG. 5.

FIGS. 40 and 41 are views for describing the arrangement of cosmetic ingredients according to a spacer.

FIGS. 42 and 43 are views for describing a position of the spacer of the ultrasound mask according to the embodiment.

FIGS. 44 and 45 are side views of an ultrasound mask according to another embodiment.

MODES OF THE INVENTION

Hereinafter, embodiments of the present invention will be described in detail with reference to the accompanying drawings. However, the spirit and scope of the present invention is not limited to a part of the embodiments described, and may be implemented in various other forms, and within the spirit and scope of the present invention, one or more of the elements of the embodiments may be selectively combined and replaced.

In addition, unless expressly otherwise defined and described, the terms used in the embodiments of the present invention (including technical and scientific terms may be construed the same meaning as commonly understood by one of ordinary skill in the art to which this invention belongs, and the terms such as those defined in commonly used dictionaries may be interpreted as having a meaning that is consistent with their meaning in the context of the relevant art.

In addition, the terms used in the embodiments of the present invention are for describing the embodiments and are not intended to limit the present invention. In this specification, the singular forms may also include the plural forms unless specifically stated in the phrase, and may include at least one of all combinations that may be combined in A, B, and C when described in "at least one (or more) of A (and), B, and C".

Further, in describing the elements of the embodiments of the present invention, the terms such as first, second, A, B, (A, and (b) may be used. These terms are only used to distinguish the elements from other elements, and the terms are not limited to the essence, order, or order of the elements.

In addition, when an element is described as being "connected", "coupled", or "connected" to another element, it may include not only when the element is directly "connected" to, "coupled" to, or "connected" to other elements, but also when the element is "connected", "coupled", or "connected" by another element between the element and other elements.

Further, when described as being formed or disposed "on (over)" or "under (below)" of each element, the "on (over)" or "under (below)" may include not only when two elements are directly connected to each other, but also when one or more other elements are formed or disposed between two elements.

Furthermore, when expressed as "on (over)" or "under (below)", it may include not only the upper direction but also the lower direction based on one element.

Hereinafter, an ultrasound mask according to embodiments will be described with reference to the drawings.

FIG. 1 is a view illustrating an ultrasound mask according to an embodiment.

Referring to FIG. 1, an ultrasound mask 1000 according to an embodiment may be formed to correspond to a shape of human face. In detail, the ultrasound mask may have a shape corresponding to the shape of human face to deliver cosmetic ingredients such as cosmetics or drugs formed on one surface of the ultrasound mask to the human facial skin.

The ultrasound mask 1000 may be provided in a predetermined size to cover a user's face and may have a predetermined elasticity in order to be adhered to the user's face. The ultrasound mask 1000 may include one surface in contact with a user's skin and the other surface opposite to the one surface, and the one surface of the ultrasound mask 1000 may be made of a material that is harmless to the human body, so that it is harmless despite being in contact with the user's skin for a long time.

The ultrasound mask 1000 may include an opening 1010 and/or a cutout portion 1020. In detail, the opening 1010 may be formed in a portion corresponding to the user's eyes or mouth. The opening 1010 is a region penetrating through one surface and the other surface of the mask 1000, and when the user wears the mask 1000, the user's eyes and mouth may be inserted into the opening 1010, and the region excluding the opening 1010 may be closely adhered to the user's face.

In addition, the cutout portion 1020 may be formed in a portion corresponding to both cheek lines, chin, and the like, which are relatively curved in order to improve adhesion between the mask 1000 and the skin. The cutout portion 1020 may have a form in which one surface and the other surface of the mask 1000 are partially cut.

The ultrasound mask may be attached to a human face to deliver cosmetic ingredients such as cosmetics or drug substances to a human facial region with which the mask is in contact.

For example, the ultrasound mask may be directly adhered to the skin of the human body, and cosmetic substances applied in advance to the skin may be easily delivered to the epidermal layer through the stratum corneum of the skin by ultrasonic waves generated from the ultrasound mask.

That is, the ultrasound mask forms a path through which a substance moves to the skin of the human body through ultrasonic waves, and thus, a substance to be absorbed into the skin may be easily transferred into the skin to be absorbed into the skin.

In detail, the mask according to the embodiment may deliver cosmetic substances or drug substances to a region of the human body that is in contact with the mask using a sonophoresis principle.

The sonophoresis principle is a means of delivering cosmetic ingredients or drug ingredients using ultrasonic waves. In detail, the sonophoresis principle is defined that microbubbles inside the skin are expanded by ultrasonic waves to form micro-channels in the skin so as to enable to absorb polar and non-polar particles and macromolecules within 5 μm.

That is, in the ultrasound mask according to the embodiment, ultrasonic waves are applied in a direction of the skin of the human body by a piezoelectric member inside the mask, and ingredients such as cosmetic substances positioned on one surface of the ultrasound mask facing the skin of the human body may pass through the stratum corneum of the skin through microchannels of the skin formed by the ultrasonic waves to be delivered to the epidermal layer.

Meanwhile, the ultrasound mask according to the embodiment described below relates to an ultrasound mask that may absorb ingredients such as cosmetic substances into the skin in a simple manner using a mask method, minimize the loss of ultrasonic waves to improve drug delivery efficiency, and minimize damage to electrodes inside the mask due to wearing the mask.

Hereinafter, Referring to FIGS. 2 to 9, an ultrasound mask according to an embodiment will be described in detail through an internal structure of a mask according a first embodiment.

FIG. 2 is a view illustrating a cross-sectional view of an ultrasound mask according to an embodiment. Referring to FIG. 2, the ultrasound mask according to the embodiment may include a plurality of piezoelectric members 500 disposed to be spaced apart from each other.

The piezoelectric member 500 may generate ultrasonic waves, and the ultrasonic waves may easily penetrate cosmetic ingredients disposed between the ultrasound mask and the skin of the human body into the skin through electrodes, wirings, and base layers serving as a specific functional layer to be described below.

In detail, referring to FIGS. 3 and 4, the plurality of piezoelectric members 500 of the ultrasound mask according to the first embodiment may be connected to each other through a plurality of wirings. In detail, a lower surface of the piezoelectric member 500 may be connected to a first wiring 210, and an upper surface of the piezoelectric member 500 may be connected to a second wiring 220.

FIG. 3 is a view for describing electrical connection between the first wiring 210 and the piezoelectric member 500 disposed on a first substrate 110 that is a lower substrate of the ultrasound mask according to the first embodiment, and FIG. 4 is a view for describing electrical connection between the second wiring 220 and the piezoelectric member 500 disposed on a second substrate 120 that is an upper substrate of the ultrasound mask according to the first embodiment.

Referring to FIG. 3, the first wiring 210 may be disposed on one surface of the first substrate 110. In detail, the first wiring 210 may be disposed on an upper surface of the first substrate 110. In more detail, the first wiring 210 may be disposed inside the first substrate 110.

The first wiring 210 may be disposed to extend in a first direction. The first wiring 210 may be arranged in the first direction. That is, the first wiring 210 may include a plurality of unit wirings extending in the first direction. For example, the first wiring 210 may include a plurality of unit wirings extending in a column direction, and the unit wirings may be disposed to be spaced apart from each other.

In detail, one end and the other end of each piezoelectric member 500 may be connected to two interconnection wirings, and the unit wirings may be defined as an assembly of interconnection wirings connected to each other.

In addition, the first wiring 210 may be defined as an assembly of a plurality of unit wirings extending in a column direction and spaced apart from each other.

In addition, referring to FIG. 4, the second wiring 220 may be disposed on one surface of the second substrate 120. In detail, the second wiring 220 may be disposed on a lower surface of the second substrate 120. In more detail, the second wiring 220 may be disposed inside the second substrate 120.

The second wiring 220 may be disposed to extend in a second direction. The second wiring 220 may be arranged in a second direction. The second direction may be a different direction from the first direction. For example, the first direction and the second direction may be directions crossing each other.

That is, the second wiring 220 may include a plurality of unit wirings extending in the second direction. As an example, the second wiring 220 may include the plurality of unit wirings extending in a row direction, and the unit wirings may be disposed to be spaced apart from each other.

In detail, one end and the other end of each piezoelectric member 500 may be connected to two interconnection wirings, and the unit wirings may be defined as the assembly of the interconnection wirings connected to each other.

In addition, the second wiring 110 may be defined as an assembly of the plurality of unit wirings extending in a row direction and spaced apart from each other.

At least one of the first wiring 210 and the second wiring 220 may include a conductive material. As an example, at least one of the first wiring 210 and the second wiring 220 may include various metals.

In detail, at least one of the first wiring 210 and the second wiring 220 may include at least one metal of chromium (Cr), nickel (Ni), copper (Cu), aluminum (Al), silver (Ag), molybdenum (Mo), gold (Au), titanium (Ti), and alloys thereof.

In addition, the first wiring 210 and the second wiring 220 may have a predetermined thickness and line width. For example, the line width of the first wiring 210 and the second wiring 220 may be 50 μm to 500 μm.

Further, the thickness of the first wiring 210 and the second wiring 220 may have a size of about 1/10 or less of the line width. As an example, the thickness of the first wiring 210 and the second wiring 220 may be about 5 μm to 50 μm.

Accordingly, when the ultrasound mask is bent or folded in one direction, it is possible to prevent the wirings from being disconnected or damaged by controlling the line width and thickness of the first wiring 210 and the second wiring 220, thereby improving the reliability of the ultrasound mask.

In addition, at least one of the first wiring 210 and the second wiring 220 may have stretch characteristics. In detail, the first wiring 210 and the second wiring 220 may have an elongation characteristic extending in a tensile direction.

For example, the first wiring 210 and the second wiring 220 may be stretched by about 10% to about 50% of the total length.

At least one of the first wiring 210 and the second wiring 220 may have a curved shape. In detail, at least one of the first wiring 210 and the second wiring 220 may extend while having a curvature.

As shown in FIGS. 3 and 4, the first wiring 210 may be arranged in the first direction while having a curvature, and the second wiring 220 may also be arranged in the second direction while having a curvature.

In the first wiring 210 and the second wiring 220, patterns having the same curvature size may be continuous, or the first wiring 210 and the second wiring 220 may extend respectively while patterns having different curvature sizes are continuous.

In detail, the first wiring 210 may extend in the first direction while patterns having a curvature size (mm) of 5R to 15R are continuous, and the second wiring 220 may extend in the second direction while patterns having a curvature size (mm) of 5R to 15R are continuous.

As the first wiring 210 and the second wiring 220 are formed in a curved shape having a curvature, it is possible to prevent the first wiring 210 and the second wiring 220 from being deformed or damaged due to stress generated when the ultrasound mask according to the first embodiment is stretched or restored.

That is, when the ultrasound mask according to the first embodiment is stretched or restored, the first wiring 210 and the second wiring 220 having a shape of continuous curvature patterns are stretched or restored together like a spring, and thus, it is possible to minimize a stress effect due to stretch or restoration.

In addition, since the first wiring 210 extends only in the first direction and the second wiring extends only in the second direction, restrictions depending on the direction may be minimized when the ultrasound mask according to the first embodiment is stretched or restored. That is, it is possible to improve the flexibility of the ultrasound mask.

FIG. 5 is a view illustrating that the first substrate 110 and the second substrate 120 overlap each other.

Referring to FIG. 5, the first substrate 110 and the second substrate 120 may be disposed to overlap in upper and lower portions, and the first wiring 210 disposed on the upper surface of the first substrate 110 and the second wiring 220 disposed on the lower surface of the second substrate 120 may also be disposed to overlap each other.

When viewed from the lower surface of the first substrate 110 or the upper surface of the second substrate 120, the first wiring 210 and the second wiring 220 may be formed in a mesh shape. That is, while the first wiring 210 extending in the first direction and the second wiring 220 extending in the second direction overlap each other, the first wiring 210 and the second wiring 220 may be formed in the mesh shape as a whole.

Hereinafter, the overall configuration of the ultrasound mask according to the first embodiment will be described in detail with reference to FIGS. 6 and 7.

FIG. 6 is a view illustrating an overall cross-sectional view taken along line B-B' in FIG. 5 of the ultrasound mask according to the first embodiment, and FIG. 7 is a view illustrating an overall cross-sectional view taken along line C-C' in FIG. 5 of the ultrasound mask according to the first embodiment.

Referring to FIGS. 6 and 7, the ultrasound mask according to the first embodiment may include a substrate, a wiring, an electrode, a piezoelectric member, and a base layer.

The substrate may include the first substrate 110 and the second substrate 120. The first substrate 110 may be the lower substrate of the ultrasound mask according to the first embodiment, and the second substrate 120 may be the upper substrate.

The first substrate 110 may support the first wiring 210 and a first electrode 410 disposed inside the first substrate 110, and the second substrate 120 may support the second wiring 220 and a second electrode 420 disposed inside the substrate 120. That is, the first substrate 110 and the second substrate 120 may be supporting substrates.

The second substrate 120 may be disposed on the upper surface of the first substrate 110. The first substrate 110 and the second substrate 120 may be disposed to be spaced apart from each other. The first substrate 110 and the second substrate 120 may be disposed to be spaced apart from each other, and the piezoelectric member 500 may be disposed between the first substrate 110 and the second substrate 120.

The first substrate 110 and the second substrate 120 may be flexible. In detail, the first substrate 110 and the second substrate 120 may be flexible so as to be bendable or foldable. In addition, at least one of the first substrate 110 and the second substrate 120 is closely adhered to the human face described above, and thus the substrate may be formed of a material harmless to the human body.

For example, the first substrate 110 and the second substrate 120 may include plastic. As an example, the first substrate 110 and the second substrate 120 may include a flexible plastic such as polyimide (PI), polyethylene terephthalate (PET), propylene glycol (PPG) polycarbonate (PC), or the like.

Accordingly, when the user wears the ultrasound mask on the face or the like and applies a deformation that stretches or restores the ultrasound mask according to the size and shape of the user's face, the shape of the ultrasound mask may be easily changed.

In addition, the first substrate 110 and the second substrate 120 may have a certain thickness.

For example, the first substrate 110 and the second substrate 120 may have a thickness of about 0.5 μm to about 5 μm or less. When the thicknesses of the first substrate 110 and the second substrate 120 are less than about 0.5 μm, shapes of the regions of the first substrate 110 and the second substrate 120 overlapping the components are changed by the weight of components to be disposed on the first substrate 110 and the second substrate 120, for example, the piezoelectric member 500, so that a problem that may affect adhesion and absorption of cosmetic ingredients may occur.

Accordingly, reliability of the first substrate 110 and the second substrate 120 may be deteriorated, and an alignment tolerance of components disposed on the first substrate 110 and the second substrate 120 may be increased.

In addition, when the thicknesses of the first substrate 110 and the second substrate 120 exceed about 5 μm, the overall thickness of the ultrasound mask 1000 according to the first embodiment may be increased. Accordingly, there is a problem that the ultrasound mask 1000 according to the first embodiment may not be efficiently varied according to the shape of the user's skin, and thus the mask 1000 does not effectively adhere to the user's skin.

Preferably, the first substrate 110 and the second substrate 120 may have a thickness of about 0.5 μm to about 3 μm. When the thicknesses of the first substrate 110 and the second substrate 120 satisfy the above-described range, the first substrate 110 and the second substrate 120 may be efficiently varied in a form corresponding to the user's skin and the overall thickness and weight of the ultrasound mask 1000 according to the embodiment may be reduced while maintaining reliability and alignment characteristics.

Meanwhile, the first substrate 110 and the second substrate 120 may have a plurality of engraved portions I and a plurality of embossed portions E. Each of the embossed portions E may be formed between the engraved portions I.

In detail, referring to FIGS. 8 and 9, a plurality of first engraved portions I1 formed on the upper surface of the first substrate 110 may be formed on the first substrate 110, and a plurality of second engraved portions I2 formed on the lower surface of the second substrate 120 may be formed on the second substrate 120.

That is, a thickness of the first substrate 110 in a region where the first engraved portion I1 is formed may be smaller than a thickness of the first substrate 110 in a region where the first engraved portion I1 is not formed.

In addition, a thickness of the second substrate 120 in a region where the second engraved portion I2 is formed may be smaller than a thickness of the second substrate 120 in a region where the second engraved portion I2 is not formed.

The first wiring 210 and the second wiring 220 described above may be disposed on the upper surface of the first substrate 110 and the lower surface of the second substrate 120, respectively.

The first wiring 210 may be disposed inside the first engraved portion I1 of the first substrate 110. In detail, the first wiring 210 may be formed while filling the inside of the first engraved portion I1 formed on the upper surface of the first substrate 110. Accordingly, the first wiring 210 may be disposed inside the first substrate 110.

In addition, the second wiring 220 may be disposed inside the second engraved portion I2 of the second substrate 120. In detail, the second wiring 220 may be formed while filling the inside of the second engraved portion I2 formed on the lower surface of the second substrate 120. Accordingly, the second wiring 220 may be disposed inside the second substrate 120.

As described above, since the first wiring 210 is formed to extend only in the first direction, and the second wiring 220 is formed to extend only in the second direction, in FIG. 6 which is a view taken along line B-B' in FIG. 5, only the curve-shaped second wiring 220 may be disposed between the piezoelectric members 500, and in FIG. 7 which is a view taken along line C-C' in FIG. 5, only the curve-shaped first wiring 210 may be disposed between the piezoelectric members 500.

Since the first wiring 210 and the second wiring 220 are disposed inside the first engraved portion I1 and the second engraved portion I2 formed in the first substrate 110 and the second substrate 120, respectively, it is possible to prevent an increase in the thickness of the ultrasound mask due to the thicknesses of the first wiring 210 and the second wiring 220.

In addition, since the first wiring 210 and the second wiring 220 are disposed while being fixed by the engraved portion inside the engraved portions, a phenomenon that the wirings are de-filmed during variable such as stretching or restoring the ultrasound mask is prevented, thereby improving the reliability of the ultrasound mask.

The piezoelectric member 500 may be disposed between the first substrate 110 and the second substrate 120. That is, the piezoelectric member 500 may be disposed on the upper surface of the first substrate 110 and may be disposed under the lower surface of the second substrate 120.

The piezoelectric member 500 may generate ultrasonic waves, and the ultrasonic waves generated from the piezoelectric member 500 may be moved from the first substrate 110 toward the second substrate 120.

The piezoelectric member 500 may be disposed between the first substrate 110 and the second substrate 120 in plural. In detail, the piezoelectric members 500 may be disposed to be spaced apart from each other between the first and second substrates 110 and 120, and accordingly, the ultrasonic waves may be generated over the entire area of the ultrasound mask.

Meanwhile, the piezoelectric members 500 may be disposed to be spaced apart at the same or a similar distance between the first substrate 110 and the second substrate 120.

Alternatively, the piezoelectric members 500 may be disposed to be spaced apart from each other at different distances between the first substrate 110 and the second substrate 120. For example, when the ultrasound mask is put on the skin of the human body, the separation distance of the piezoelectric member 500 may vary depending on a size at which the ultrasound mask is bent.

For example, when the ultrasound mask is put on the skin of the human body, a bent region for each region may vary depending on the shape and size of the face. In this case, the distance of the piezoelectric member 500 may be increased in the region where the ultrasound mask is bent, and accordingly, the distance of the piezoelectric member 500 is decreased in a region that is largely bent, so that it is possible to compensate that the distance of the piezoelectric element is varied for each region when the ultrasound mask is put on the skin.

Meanwhile, the piezoelectric member 500 may include a rigid material.

The piezoelectric member 500 may include various piezoelectric materials. For example, the piezoelectric member 500 may include single crystal ceramics, polycrystalline ceramics, a polymer material, a thin film material, or a composite material in which the polycrystalline material and the polymer material are composited.

A piezoelectric material of the single crystal ceramics may include α-AlPO4, α-SiO2, LiTiO3, LiNbO3, SrxBayNb2O3, Pb5-Ge3O11, Tb2(MnO4)3, Li2B4O7, CdS, ZnO, Bi12SiO20, or Bi12GeO20.

In addition, a piezoelectric material of the polycrystalline ceramics may include PZT-based, PT-based, PZT-Complex Perovskite-based, or BaTiO3.

In addition, a piezoelectric material of the polymer material may include PVDF, P(VDF-TrFe), P(VDFTeFE), or TGS.

In addition, a piezoelectric material of the thin film material may include ZnO, CdS, or AlN.

In addition, a piezoelectric material of the composite material may include PZT-PVDF, PZT-Silicon Rubber, PZT-Epoxy, PZT-foaming polymer, or PZT-foaming urethane.

The plurality of piezoelectric members 500 may include at least one piezoelectric material among the single crystal ceramics, the polycrystalline ceramics, the polymer material, the thin film material, or the composite material in which the polycrystalline material and the polymer material are composited.

The plurality of piezoelectric members 500 may include the same piezoelectric material or may include different piezoelectric materials.

For example, the ultrasound mask according to the embodiment may include a piezoelectric material that generates low-frequency or medium-frequency ultrasonic waves. In detail, the ultrasound mask according to the embodiment may include a piezoelectric material that generates ultrasonic waves of a low frequency having a 20 kHz to 100 kHz band and/or a medium frequency having a 100 kHz to 1 MHz band that are optimized for beauty.

As an example, the ultrasound mask according to the embodiment may include single crystal or polycrystalline ceramics including ceramic.

The waveform of the ultrasonic wave applied from the piezoelectric member 500 is not limited and may include a sine waveform, a sawtooth waveform, or a pulse waveform.

In addition, ultrasonic waves generated from the piezoelectric member 500 may be applied as at least one of a transverse wave and a longitudinal wave. In detail, the ultrasonic waves generated from the piezoelectric member 500 may be applied as a single wave of a transverse wave, a single wave of a longitudinal wave, or a plurality of waves applied with both transverse wave and longitudinal wave.

That is, the piezoelectric member according to the embodiment may generate the ultrasonic waves in a single or multiple resonance modes.

A thickness of the piezoelectric member 500 may be about 600 μm or less. In detail, the thickness of the piezoelectric member 500 may be about 500 μm or less. Preferably, the thickness of the piezoelectric member 500 may be about 300 μm or less. It is preferable that the thickness of the piezoelectric member 500 satisfies the above-described range in consideration of the variable characteristics of the ultrasound mask 1000.

The piezoelectric member 500 may have various shapes. For example, the piezoelectric member 500 may have a polygonal column shape in which lower and upper surfaces are polygonal, and the lower and upper surfaces may have a circular column shape. In addition, one surface of the lower and upper surfaces of the piezoelectric member 500 may be a polygon and the other surface may have a pillar shape. As an example, an area of at least one of the lower surface and the upper surface of the piezoelectric member 500 may be about 100 mm² or less.

As described above, the piezoelectric member 500 may have various pillar shapes, and intensity of ultrasonic vibration and an oscillation direction of vibration generated according to the pillar shape may be controlled. In addition, the intensity of vibration transmitted to the user's skin may be adjusted according to a size, arrangement interval, arrangement density, and the like of the piezoelectric member 500.

The piezoelectric member 500 may generate various waves. For example, the piezoelectric member 500 may generate at least one wave of a transverse wave in which a traveling direction of wave and a vibration direction of medium are perpendicular, and a longitudinal wave in which the traveling direction of wave and the vibration direction of medium are the same. In addition, the piezoelectric member 500 may multiple-resonate.

For example, the piezoelectric member 500 may include at least one via hole and may multiple-resonate by the formed via holes. In this case, an upper area of the via holes may be about 10% to about 45% of an area of the upper surface of the piezoelectric member 500 for multiple resonance.

In addition, when the piezoelectric member 500 multiple-resonates by the via holes, the number of multiple resonance frequency regions may correspond to the number of the via holes. That is, the piezoelectric member 500 may emit wavelengths of various frequency ranges as the number of the via holes increases in a set number range of via holes.

An electrode may be disposed on the lower surface and the upper surface of the piezoelectric member 500, respectively. In detail, the first electrode 410 may be disposed on the lower surface of the piezoelectric member 500, and the second electrode 420 may be disposed on the upper surface of the piezoelectric member 500.

That is, the first electrode 410 may be disposed on the upper surface of the first substrate 110, and the second electrode 420 may be disposed under the lower surface of the second substrate 120.

The first electrode 410 and the second electrode 420 may be in contact with the piezoelectric member 500. In detail, the first electrode 410 may be disposed in direct contact with the lower surface of the piezoelectric member 500, and the second electrode 420 may be disposed in direct contact with the upper surface of the piezoelectric member 500.

Accordingly, the first electrode 410 and the second electrode 420 may be disposed on both surfaces of the piezoelectric member 500, respectively, and a voltage may be applied to the piezoelectric member by the first electrode 410 and the second electrode 420 to vibrate the piezoelectric member.

In detail, a voltage applied from the outside of the ultrasound mask is transmitted to the first electrode 410 and the second electrode 420 through the first wiring 210 and the second wiring 220, and accordingly, the voltage is applied to the piezoelectric member 500, so that the piezoelectric member 500 may be vibrated to generate ultrasonic waves having a specific frequency range.

The first electrode 410 may be disposed on the entire surface of the lower surface of the piezoelectric member 500. In addition, the second electrode 420 may be disposed on the entire surface of the upper surface of the piezoelectric member 500. In this case, the entire surface of the lower surface and the upper surface of the piezoelectric member may be defined as a region including an error during the process.

At least one of the first electrode 410 and the second electrode 420 may include various metals. For example, at least one of the first electrode 410 and the second electrode 420 may include at least one metal of chromium (Cr), nickel (Ni), copper (Cu), aluminum (Al), silver (Ag), molybdenum (Mo), gold (Au), titanium (Ti), and alloys thereof.

Alternatively, at least one of the first electrode 410 and the second electrode 420 may be formed in a mesh shape. In detail, at least one of the first electrode 410 and the second electrode 420 may include a plurality of sub-electrodes, and the sub-electrodes may be disposed to cross each other in the mesh shape.

In detail, at least one of the first electrode 410 and the second electrode 420 may include a mesh line LA and a mesh opening OA between the mesh lines LA by the plurality of sub-electrodes crossing each other in the mesh shape.

A line width of the mesh line LA may be about 0.1 µm to about 10 µm. A mesh line having a line width of less than about 0.1 µm of the mesh line LA may not be possible in a manufacturing process, and when the line width exceeds about 10 µm, an electrode pattern may be visually recognized from the outside and visibility may be reduced. In detail, the line width of the mesh line LA may be about 1 µm to about 5 µm. In more detail, the line width of the mesh line LA may be about 1.5 µm to about 3 µm.

In addition, the thickness of the mesh line LA may be about 100 nm to about 1000 nm. When the thickness of the mesh line is less than about 100 nm, an electrode resistance may increase and electrical characteristics may be deteriorated. When the thickness of the mesh line exceeds about 1000 nm, the overall thickness of the ultrasound mask may increase and process efficiency may be deteriorated. In detail, the thickness of the mesh line LA may be about 150 nm to about 500 nm. In more detail, the thickness of the mesh line LA may be about 180 nm to about 200 nm.

In addition, the mesh opening may be formed in various shapes. For example, the mesh opening OA may have various shapes such as a square shape, a diamond shape, a polygonal shape of pentagonal shape and hexagonal shape, a circular shape, or the like. In addition, the mesh opening may be formed in a regular shape or a random shape.

The electrode and the wiring may be adhered to each other. In detail, the electrode and the wiring may be adhered to each other through a conductive adhesive layer.

In detail, the first wiring 210 and the first electrode 410 may be adhered through a first adhesive layer 310, and the second wiring 210 and the second electrode 420 may be adhered through a second adhesive layer 320.

The first adhesive layer 310 and the second adhesive layer 320 may have conductivity. In detail, the first adhesive layer 310 and the second adhesive layer 320 may be conductive pastes. For example, the first adhesive layer 310 and the second adhesive layer 320 may include silver (Ag) paste.

Accordingly, the first wiring 210 and the first electrode 410 and the second wiring 220 and the second electrode 420 may be electrically connected to by the first adhesive layer 310 and the second adhesive layer 320.

Meanwhile, the first adhesive layer 310 and the second adhesive layer 320 may be formed to have the same and similar thickness. Alternatively, the first adhesive layer 310 and the second adhesive layer 320 may be formed to have different thicknesses.

In detail, a thickness of the first adhesive layer 310 may be greater than a thickness of the second adhesive layer 320. That is, the thickness of the first adhesive layer 310 disposed further from the skin may be greater than the thickness of the second adhesive layer 320.

Accordingly, ultrasonic waves generated from the piezoelectric member 500 and moved in a opposite direction of the skin may be reflected by the first adhesive layer 310 to transmit in a direction of the skin by making a thickness of the first adhesive layer 310 different from a thickness of the second adhesive layer 320, thereby minimizing the loss of ultrasonic waves.

Meanwhile, base layers for easily transmitting ultrasonic waves to the skin may be disposed on outer surfaces of the first substrate 110 and the second substrate 120, respectively.

The above-described substrates, wirings, electrodes, and piezoelectric members may be disposed between the base layers, that is, the base layers may be support layers supporting a plurality of components.

For example, when it is defined that a position where the second substrate 120 is disposed is a place close to the skin of the human body, and a position where the first substrate 110 is disposed is a place far from the skin of the human body, a first base layer 610 in which the ultrasonic waves generated from the piezoelectric member 500 is reflected so that the ultrasonic waves are transmitted in the direction of the skin of the human body may be disposed on an outer surface of the first substrate 110, that is, the lower surface of the first substrate 110.

A second base layer 620 in which the ultrasonic waves generated from the piezoelectric member 500 is reflected so that the ultrasonic waves are transmitted in the direction of the skin of the human body may be disposed on an outer surface of the second substrate 120, that is, the upper surface of the second substrate 120. That is, the second base layer 620 may be defined as a layer that is in direct contact with the skin of the human body to transmit the ultrasonic waves.

In detail, the second base layer 620 may be disposed on the upper surface of the second substrate 120. The second base layer 620 may include a matching layer.

The second base layer 620 may reduce energy loss due to reflection of an ultrasonic signal due to a difference in acoustic impedance between the piezoelectric member and the object, that is, the skin of the human body. To this end, the second base layer 620 is formed of a material having an acoustic impedance corresponding to between the acoustic impedance of the piezoelectric member and the acoustic impedance of the skin of the human body, and accordingly, energy loss of the ultrasonic signal may be minimized by configuring a plurality of acoustic matching layers having an acoustic impedance gradually decreasing from the second base layer 620 adjacent to the piezoelectric element.

As an example, the second base layer 620 may include silicon (Si). For example, the second base layer 620 may include silicon or a silicon compound. In addition, a thickness of the second base layer 620 may be about 1 mm or less. In detail, a thickness of the matching layer may be about 300 μm to about 1 mm.

The thickness of the second base layer 620 may be changed depending on the frequency of ultrasonic waves generated from the piezoelectric member 500.

In detail, the thickness of the second base layer 620 may be defined as a size of λ/4 or more of the wavelength at the wavelength λ calculated by the following equation.

$$\text{Sound velocity of the second base layer} = \text{Frequency generated from the piezoelectric member} * \text{wavelength} (\lambda) \quad \text{[Equation]}$$

That is, the thickness of the second base layer 620 may be formed so as to have a size of about 25% or more of the size of the wavelength calculated by the equation.

For example, when the second base layer 620 includes silicon (Si), a wavelength value may be determined depending on a size of the frequency region generated in the piezoelectric member, and the thickness of the second base layer 620 may be formed in a size of about 25% or more of the size of the wavelength.

Accordingly, when ultrasonic waves generated from the piezoelectric member are transmitted to the human skin by the matching layer, the loss of ultrasonic waves may be minimized.

The first base layer 610 may be disposed on the lower surface of the first substrate 110. The first base layer 610 may include a backing layer.

The first base layer 610 may reflect the ultrasonic waves moving in a direction of the first substrate that is a direction opposite to the skin of the human body among the ultrasonic waves generated from the piezoelectric member 500 and moving in the direction of the skin of the human body. That is, the first base layer 610 may be a reflective layer that reflects the ultrasonic waves.

The backing layer may include a material the same as or similar to that of the matching layer. For example, the backing layer may include silicon (Si).

The backing layer may be formed with a thickness different from that of the matching layer. In detail, the backing layer may be formed to have a thickness the same as or smaller than that of the matching layer.

In addition, the first base layer 610 may have an air layer formed therein to easily reflect the ultrasonic waves. That is, a plurality of pores may be formed inside the first base layer 610 to reflect the ultrasonic waves incident into the first base layer 610 toward the second base layer 620.

In addition, the first base layer 610 may be formed in a shape different from that of the second base layer 620. In detail, the first base layer 610 may include a groove formed in a region corresponding to the piezoelectric member 500. Accordingly, the ultrasonic waves incident into the first base layer 610 may be reflected toward the second base layer 620 by the air layer formed inside the groove.

The first base layer 610 and the second base layer 620 may be formed to have a size the same as or similar to that of the first base layer 110 and the second base layer 120. That is, the first base layer 610 and the second base layer 620 may be disposed while covering the plurality of piezoelectric members.

That is, the first base layer 610 and the second base layer 620 are formed to be greater than an area of the piezoelectric member, so that ultrasonic waves radiated from the piezoelectric member may be effectively transmitted in the direction of the skin of the human body.

Accordingly, the ultrasonic waves generated radially from the piezoelectric material may be easily transmitted in the direction of the skin of the human body by the first base layer and the second base layer.

Meanwhile, a protective layer 150 may be disposed between the first substrate 110 and the second substrate 120. The protective layer 150 may include a material that is the same as or similar to that of at least one of the first base layer 610 and the second base layer 620. For example, the protective layer 150 may include silicon or a silicon-based compound.

The first wiring 210 and the second wiring 220 may be in contact with the protective layer 150. In detail, a part of the first wiring 210 and the second wiring 220 may be in contact with the protective layer 150.

In detail, an interconnection wiring of the first wiring 210 and the second wiring 220 connecting the piezoelectric members 500 may be in contact with the protective layer 150.

That is, the interconnection wirings of the first wiring 210 and the second wiring 220 may be disposed in the engraved portions of the first substrate 110 and the second substrate 120, respectively, an exposed surface may be formed in which one surface of the interconnection wiring is exposed to the outside, and the exposed surface of the interconnection wiring may be in contact with the protective layer 150.

The protective layer 150 prevents damage from external impacts or impurities to the piezoelectric member 500, the electrodes, the wirings, and the like between the first substrate 110 and the second substrate 120, thereby improving the reliability of the ultrasound mask.

In addition, as the protective layer 150 is disposed while covering the interconnection wirings of the first and second wirings exposed to the outside, oxidation of the wirings including the metal may be prevented, thereby improving reliability.

The ultrasound mask according to the first embodiment may easily transfer a material into the skin of the human body using ultrasonic waves.

In detail, cosmetic substances such as cosmetics may be easily delivered according to a position, shape, and size of an object to be worn by a user through a rigid piezoelectric member, a flexible substrate, and a wiring.

In addition, when the user wears the ultrasound mask through the substrate and the wiring that may be stretched and restored, it is possible to prevent an electrode from being damaged due to deformation of the ultrasound mask.

In addition, it is possible to minimize the loss of ultrasonic waves generated during transmission by controlling the directionality of the ultrasonic waves generated from the piezoelectric member by the matching layer and the backing layer.

In addition, it is possible to minimize the loss of ultrasonic waves generated during transmission by controlling thicknesses of the matching layer and the backing layer and controlling the movement of ultrasonic waves according to the frequency band of the ultrasonic waves generated from the piezoelectric member.

In addition, when the ultrasound mask is stretched or restored, the first wiring 210 and the second wiring 220 having a shape of continuous curvature patterns are stretched or restored together like a spring, so the stress effect due to stretch or restoration may be minimized.

In addition, since the first wiring 210 extends only in the first direction and the second wiring extends only in the second direction, when the ultrasound mask according to the first embodiment is stretched or restored, the restriction depending on the direction may be minimized. That is, the flexibility of the ultrasound mask may be improved.

Hereinafter, an ultrasound mask according to a second embodiment will be described with reference to FIGS. 10 to 14. In the description of the ultrasound mask according to the second embodiment, a description of the same and similar description as the ultrasound mask according to the first embodiment described above will be omitted. In addition, in the description of the ultrasound mask according to the second embodiment, the same reference numerals are given to the same components as those of the ultrasound mask according to the first embodiment described above.

Referring to FIGS. 10 to 14, the ultrasound mask according to the second embodiment may have different directions in which the first and second wirings extend from the ultrasound mask according to the first embodiment described above.

In detail, referring to FIG. 10, the first wiring 210 may be disposed on the upper surface of the first substrate 110. That is, the first wiring 210 may be disposed inside the first substrate 110. In addition, the first wiring 210 may be arranged in a first direction and a second direction that cross each other. Accordingly, the first wiring 210 may be arranged in two different directions.

That is, the first wiring 210 may include a plurality of unit wirings extending in the first direction and a plurality of unit wirings extending in the second direction. For example, the first wiring 210 may include a plurality of unit wirings extending in a row direction and a plurality of unit wirings extending in a column direction, and the unit wirings may be disposed to be spaced apart from each other.

In addition, referring to FIG. 11, the second wiring 220 may be disposed on the lower surface of the second substrate 120. That is, the second wiring 220 may be disposed inside the second substrate 120. The second wiring 220 may be formed to extend in the first direction and the second direction. That is, the second wiring 220 may be disposed to extend in two different directions, and the direction in which the second wiring 220 extends may be similar to that of the first wiring 210.

That is, the second wiring 220 may include a plurality of unit wirings extending in the first direction and a plurality of unit wirings extending in the second direction. As an example, the second wiring 220 may include a plurality of unit wirings extending in the row direction and a plurality of unit wirings extending in the column direction, and the unit wirings may be disposed to be spaced apart from each other.

That is, when viewed from the lower surface of the first substrate 110, the first wiring 210 may be formed in a mesh shape, and when viewed from the upper surface of the second substrate 120, the second wiring 220 may be formed in the mesh shape, FIG. 12 is a view illustrating that the first substrate 110 and the second substrate 120 overlap each other.

Referring to FIG. 12, the first substrate 110 and the second substrate 120 are disposed to overlap in upper and lower portions, and the first wiring 210 and the first wiring 210 disposed on the upper surface of the first substrate 110 and the second wiring 220 disposed on the lower surface of the second substrate 120 may also be disposed to overlap each other.

When viewed from the lower surface of the first substrate 110 or the upper surface of the second substrate 120, the first wiring 210 and the second wiring 220 may be formed in the mesh shape. That is, while the first wiring 210 extending in the first direction and the second wiring 220 extending in the second direction overlap each other, the first wiring 210 and the second wiring 220 may be formed in the mesh shape as a whole.

In the ultrasound mask according to the second embodiment, the first wiring may be formed to extend in two directions, and the second wiring may also be arranged in two directions.

Accordingly, both the first wiring 210 and the second wiring 220 may be arranged in two different directions in the first direction and the second direction.

Therefore, in FIG. 13 which is a view taken along line D-D' in FIG. 12, both the first wiring 210 and the second wiring 220 having the curved shape are disposed between the piezoelectric members 500, and in FIG. 14 which is a view taken along line E-E' in FIG. 12, both the first wiring 210 and the second wiring 220 having the curved shape are disposed between the piezoelectric members 500.

Accordingly, even though a short circuit occurs in the first wiring or the second wiring in the row direction in one piezoelectric member 500, the first wiring or the second wiring in the column direction is energized, and even though a short circuit occurs in the first wiring or the second wiring in the column direction, the first wiring or the second wiring in the row direction is energized, so that deterioration of characteristics due to the short circuit may be prevented.

As described above, the ultrasound mask may be varied to fit the shape of the skin of the human body, and a short circuit may be generated in the wiring due to the stress generated in the changing process.

Since the ultrasound mask according to the second embodiment is arranged to extend wiring in both the row direction and the column direction, even though the wiring is shorted in one direction, it is possible to prevent an overall short circuit by the wiring extending in the other direction, and thus electrical characteristics and reliability of an ultrasonic element may be improved.

Hereinafter, an ultrasound mask according to a third embodiment will be described with reference to FIGS. 15 to 19. In the description of the ultrasound mask according to the third embodiment, a description of the same and similar description as the ultrasound mask according to the first and second embodiments described above will be omitted. In addition, in the description of the ultrasound mask according to the second embodiment, the same reference numerals are given to the same components as those of the ultrasound mask according to the first and second embodiments described above.

Referring to FIGS. 15 to 19, the ultrasound mask according to the third embodiment may have different directions of the first and second wirings from the ultrasound masks according to the first and second embodiments described above.

In detail, referring to FIG. 15, the first wiring 210 may be disposed on the upper surface of the first substrate 110. That is, the first wiring 210 may be disposed inside the first substrate 110. In addition, the first wiring 210 may be arranged only in the first direction.

That is, the first wiring 210 may include a plurality of unit wirings extending in the first direction. As an example, the first wiring 210 may include a plurality of unit wirings extending in a column direction, and the unit wirings may be disposed to be spaced apart from each other.

In addition, referring to FIG. 16, the second wiring 220 may be disposed on the lower surface of the second substrate 120. That is, the second wiring 220 may be disposed inside the second substrate 120. The second wiring 220 may be arranged in the first direction and the second direction.

That is, the second wiring 220 may include a plurality of unit wirings extending in the first direction and a plurality of unit wirings extending in the second direction. As an example, the second wiring 220 may include a plurality of unit wirings extending in the row direction and a plurality of unit wirings extending in the column direction, and the unit wirings may be disposed to be spaced apart from each other.

That is, a shape of the first wiring 210 when viewed from the lower surface of the first substrate 110 and a shape of the second wiring 220 when viewed from the upper surface of the second substrate 120 may be different from each other.

FIGS. 15 and 16 illustrate that the first wiring extends in one direction and the second wiring is arranged in two directions, but the embodiment is not limited thereto, and conversely, the first wiring may be arranged in two directions, and the second wirings may be arranged in one direction.

FIG. 17 is a view illustrating that the first substrate 110 and the second substrate 120 overlap each other.

Referring to FIG. 17, the first substrate 110 and the second substrate 120 are disposed to overlap in upper and lower portions, and the first wiring 210 and the first wiring 210 disposed on the upper surface of the first substrate 110 and the second wiring 220 disposed on the lower surface of the second substrate 120 may also be disposed to overlap each other.

When viewed from the lower surface of the first substrate 110 or the upper surface of the second substrate 120, the first wiring 210 and the second wiring 220 may be formed in the mesh shape. That is, while the first wiring 210 extending in the first direction and the second wiring 220 extending in the second direction overlap each other, the first wiring 210 and the second wiring 220 may be formed in the mesh shape as a whole.

In this case, since the first wiring extends only in the column direction and the second wiring extends in the row and column directions, when viewed from the lower surface of the first substrate 110 or the upper surface of the second substrate 120, a thickness of the wiring in the column direction may appear greater than a thickness of the wiring in the row direction.

In the ultrasound mask according to the third embodiment, the first wiring may be arranged in one direction, and the second wiring may be arranged in two directions.

Accordingly, since one wiring of the first wiring 210 and the second wiring 220 extends in only one direction and the other wiring extends in two directions, even though a short circuit occurs in the first wiring or the second wiring in the row direction in one piezoelectric member 500, the first wiring or the second wiring in the column direction is energized, and the first wiring or the second wiring in the column direction is energized, and even though a short circuit occurs in the first wiring or the second wiring in the column direction, the first wiring or the second wiring in the row direction is energized, so that deterioration of characteristics due to the short circuit may be prevented.

As described above, the ultrasound mask may be varied to fit the shape of the skin of the human body, and a short circuit may be generated in the wiring due to the stress generated in the changing process.

Since the ultrasound mask according to the third embodiment is arranged to extend wiring in both the row direction and the column direction, even though the wiring is shorted in one direction, it is possible to prevent an overall short circuit by the wiring extending in the other direction, and thus electrical characteristics and reliability of an ultrasonic element.

In addition, since one wiring of the first wiring 210 and the second wiring 220 extends only in one direction and the other wiring extends in two directions, when the ultrasound mask according to the third embodiment is stretched or restored, the restriction depending on the direction may be minimized. That is, the flexibility of the ultrasound mask may be improved.

Hereinafter, ultrasound masks according to fourth to sixth embodiments will be described with reference to FIGS. 20 to 22. In the description of the ultrasound masks according to the fourth to sixth embodiments, a description of the same and similar description as the ultrasound mask according to the first to third embodiments described above will be omitted. In addition, in the description of the ultrasound masks according to the fourth to sixth embodiments, the same reference numerals are given to the same components as the ultrasound masks according to the first to third embodiments described above.

Referring to FIGS. 20 to 22, in the ultrasound masks according to the fourth to sixth embodiments, a metal layer and a cover layer may be disposed on a lower surface of the first base layer 610 or an upper surface of the second base layer 620 or the lower surface of the first base layer 610 and the upper surface of the second base layer 620.

In detail, referring to FIGS. 20 and 21, in the ultrasound masks according to the fourth and fifth embodiments, a metal layer 710 may be disposed on the lower surface of the first base layer 610 or the upper surface of the second base layer 620, and a cover layer 720 may be disposed below or above the metal layer.

In detail, referring to FIG. 20, in the ultrasound mask according to the fourth embodiment, the metal layer 710 may be disposed on the lower surface of the first base layer 610, and the cover layer 720 may be disposed on a lower surface of the metal layer 710.

In addition, referring to FIG. 21, in the ultrasound mask according to the fifth embodiment, the metal layer 710 may be disposed on the upper surface of the second base layer 620, and the cover layer 720 may be disposed on the top surface of the metal layer 710.

In addition, referring to FIG. 22, in the ultrasound mask according to the sixth embodiment, a first metal layer 711 may be disposed on the lower surface of the first base layer 610, and a first cover layer 721 may be disposed on a lower surface of the first metal layer 711. In addition, a second metal layer 712 may be disposed on the upper surface of the second base layer 620, and a second cover layer 722 may be disposed on a top surface of the second metal layer 712.

The metal layer 710 may have a certain elongation characteristic to vary the ultrasound mask. In addition, the cover layer 720 may include a material the same as or similar to that of the substrate or the protective layer. That is, the cover layer 720 may include silicon (Si).

The metal layer 710 may be disposed on the outermost surface of the ultrasound mask according to the embodiment to block the inflow of moisture and air that may penetrate from the outside. Accordingly, it is possible to prevent the electrodes and the piezoelectric member therein from being oxidized by the inflow of moisture and air into the ultrasound mask, and accordingly, it is possible to improve the reliability of the ultrasound mask. That is, the metal layer 710 may improve moisture permeability and durability of the ultrasound mask.

In addition, the cover layer 720 may be disposed on an outer surface of the metal layer 710 to prevent the metal layer 710 exposed to the outside from being corroded by reaction with air.

In addition, the metal layer may block the piezoelectric member, the electrode, or the wiring from being visually recognized from the outside, thereby improving the appearance of the ultrasound mask.

As previously explained, the piezoelectric member 500 may have multiple resonance. That is, the piezoelectric member 500 may oscillate at least three or more ultrasonic waves having different frequencies. In detail, the piezoelectric member 500 may oscillate at least three or more ultrasonic waves having different frequencies and oscillating in a flexion mode.

Referring to FIGS. 23 and 26, the piezoelectric member 500 may have a multilayer structure. In detail, the piezoelectric member 500 may be formed in a multi-layered structure including a first layer 510 and a second layer 520.

The first layer 510 may be positioned in a region facing the skin and may be in contact with the second electrode 420, and the second layer 520 may be in contact with the first electrode 410.

The first layer 510 may include a metal material. In detail, the first layer 510 may include at least one of aluminum, stainless steel (SUS), and brass. The first layer 510 may have elasticity.

In addition, the second layer 520 may include a piezoelectric material. In detail, the piezoelectric member may include a ceramic piezoelectric material such as single crystal ceramics or polycrystalline ceramics.

A piezoelectric material of the single crystal ceramics may include $\alpha$-AlPO4, $\alpha$-SiO2, LiTiO3, LiNbO3, SrxBayNb2O3, Pb5-Ge3O11, Tb2(MnO4)3, Li2B4O7, CdS, ZnO, Bi12SiO20, or Bi12GeO20.

In addition, a piezoelectric material of the polycrystalline ceramics may include PZT-based, PT-based, PZT-Complex Perovskite-based, or BaTiO3.

The plurality of piezoelectric members 500 may include at least one piezoelectric material among the single crystal ceramics and the polycrystalline ceramics. As an example, the piezoelectric member 500 may include a piezoelectric material of PZT-based polycrystalline ceramics.

The first layer 510 and the second layer 520 may be formed in a circular shape. In detail, the first layer 510 and the second layer 520 may be formed in a cylindrical shape with an outer diameter greater than a height. In addition, at least one of the first layer 510 and the second layer 520 may be formed in a ring shape in which a through-hole is formed inside a circular shape. That is, the through-hole may be formed in at least one of the first layer 510 and the second layer 520.

In other words, the first layer 510 and the second layer 520 may be formed in the circular shape, and at least one layer is formed with the through-hole, so that the first layer 510 and the second layer 520 may be formed with an outer diameter and/or an inner diameter and thickness.

The first layer 510 and the second layer 520 may implement multiple resonance in which the piezoelectric member 500 oscillates in at least three or more flexion modes by limiting the outer diameter, inner diameter, and thickness to a specific range.

Referring to FIG. 26, in the piezoelectric member 500, the first layer 510 and the second layer 520 may be formed in various shapes according to the outer diameter, the inner diameter, and the thickness.

Referring to FIG. 26A, in the piezoelectric member 500, the first layer 510 and the second layer 520 may have the same outer diameter, and a through-hole may be formed in the second layer 520. Accordingly, a frequency of the flexion mode may be formed in outer diameter portions of the first layer 510 and the second layer 520, a frequency that is in the flexion mode and has a different magnitude may be formed in the through-hole of the second layer 520, and a frequency that has a different magnitude and is in a flexion mode mixed with flexion rather than a pure thickness mode may be formed in the second layer 520.

Referring to FIG. 26B, in the piezoelectric member 500, the first layer 510 and the second layer 520 may have different outer diameters, and the through-hole may be formed in the second layer 520. Accordingly, a frequency of the flexion mode may be formed in the outer diameter portion of the first layer 510, a frequency that is in the flexion mode and has a different magnitude may be formed in the outer diameter portion of the second layer 520, and a frequency that is in the flexion mode and has a different magnitude may be formed in the through-hole of the second layer 520.

Referring to FIG. 26C, in the piezoelectric member 500, the first layer 510 and the second layer 520 may have different outer diameters, and the through-hole may be formed in each of the first layer 510 and the second layer 520. Accordingly, a frequency of the flexion mode may be formed in the outer diameter portion of the first layer 510 and the second layer 520, a frequency that is in the flexion mode and has a different magnitude may be formed in in the outer diameter portion of the first layer 510, and a frequency that is in the flexion mode and has a different magnitude may be formed in the through-hole of the second layer 520.

That is, the piezoelectric member may oscillate at least three frequencies having different sizes while having the flexion mode by controlling the outer diameter, inner diameter, and thickness of the first layer 510 and the second layer 520.

In detail, when an electric field is applied to the piezoelectric member 500, the second layer 520 of the piezoelectric member 500, that is, the piezoelectric material expands or contracts in a longitudinal direction, and the first layer 510 causes a vertical flexion displacement according to the contraction and expansion of the second layer 520.

That is, the piezoelectric member 500 may oscillate ultrasonic waves in a flexion mode in which an area resonance mode and a thickness resonance mode are combined.

As described above, in case of the thickness mode, it is advantageous to transmit ultrasound in the skin direction, but there is a problem due to an increase in thickness, and in case of the area resonance mode, the thickness problem may be solved, but it is difficult to transmit the ultrasound in the skin direction.

Accordingly, the piezoelectric member of the ultrasound mask according to the embodiment may easily transmit the ultrasound in the skin direction without the problem in thickness due to the piezoelectric member oscillating in the flexion mode.

In addition, the piezoelectric member 500 may perform multiple resonance. In detail, the piezoelectric member 500 may oscillate at least three or more frequencies having different sizes. In more detail, the piezoelectric member 500 may oscillate at least three or more frequencies having different sizes oscillating in the flexion mode.

The piezoelectric member 500 may generate a center frequency and may generate at least two or more frequencies having different sizes before and after the center frequency. For example, the piezoelectric member 500 may generate two or more frequencies having different sizes in a range of about 150 kHz before and after the center frequency. For example, the piezoelectric member 500 may have a center frequency of about 200 kHz to about 400 kHz and may generate two or more frequencies having different sizes in a range of about 150 kHz before and after the center frequency.

For example, the piezoelectric member 500 may oscillate a center frequency of 232 kHz and may oscillate frequencies of 115 kHz and 357 kHz, which are the vicinity of the center frequency. That is, the piezoelectric member 500 may oscillate a first frequency higher and a second frequency lower than the center frequency in the vicinity of the center frequency, and at this time, the center frequency and the first and second frequencies may oscillate in the flexion mode.

Therefore, the user may select a desired frequency level to use the ultrasound mask. In detail, according to the user's skin environment, a high-frequency ultrasound may be used for a thin-skinned user, and a low-frequency ultrasound may be used for a thick-skinned user.

Accordingly, since users having different skin environments and conditions may select a frequency suitable for the user to use the ultrasound mask, the efficiency of the ultrasound mask may be improved.

Meanwhile, in order for the piezoelectric member 500 to oscillate in the flexion mode and to perform multiple resonance, sizes of the inner diameter, outer diameter, and thickness of the first layer 510 and the second layer 520 constituting the piezoelectric member 500 may be controlled in a certain size range.

In detail, a thickness t1 of the first layer 510 and a thickness t2 of the second layer 520 may be about 200 μm to 1500 μm. Forming the thickness t1 of the first layer 510 and the thickness t2 of the second layer 520 to be less than about 200 μm is difficult to implement in a process, and when the thickness t1 of the first layer 510 and the thickness t2 of the second layer 520 are formed to exceed about 1500 μm, the thickness of the piezoelectric member 500 is increased, thereby increasing the overall thickness of the ultrasound mask.

In addition, the thickness t1 of the first layer may have a thickness of 80% to 120% of the thickness t2 of the second layer. That is, the thickness t1 of the first layer 510 and the thickness t2 of the second layer are the same as each other, or, a thickness of one of the first layer 510 and the second layer 520 may be greater.

In this case, when the thickness t1 of the first layer is less than 80% of the thickness t2 of the second layer, or the thickness t1 of the first layer exceeds 120% of the thickness t2 of the second layer, the frequency of the ultrasonic waves generated from the piezoelectric member 500 is increased. That is, ultrasonic waves having frequencies that are not suitable for cosmetic purposes may be generated from the ultrasound mask, and the number of frequencies oscillating in the flexion mode may be less than three.

In addition, an outer diameter R1 of the first layer 510 and an outer diameter R2 of the second layer 520 may be about 3 mm to 8 mm. In addition, the outer diameter R1 of the first layer may have a size of 92% to 108% of the outer diameter R2 of the second layer. That is, the outer diameter R1 of the first layer 510 and the outer diameter R2 of the second layer 520 are the same as each other, or an outer diameter of one of the first layer 510 and the second layer 520 may be greater.

When the outer diameter R1 of the first layer is less than 92% of the outer diameter R2 of the second layer, or the outer diameter R1 of the first layer exceeds 108% of the outer diameter R2 of the second layer, the frequency of the ultrasonic waves generated from the piezoelectric member 500 is increased. That is, ultrasonic waves having frequencies that are not suitable for cosmetic purposes may be generated from the ultrasound mask, and the number of frequencies oscillating in the flexion mode may be less than three.

In addition, an inner diameter r1 of the first layer 510 may be 0 mm to 1.5 mm (when an inner diameter is 0 mm, the first layer is not formed with a through-hole), and an inner diameter r2 of the second layer 520 may be about 1.5 mm to 5.6 mm. In addition, the inner diameter r1 of the first layer 510 may be about 20% or less of the inner diameter r2 of the second layer 520. That is, the inner diameter r1 of the first layer 510 may be smaller than the inner diameter r2 of the second layer 520.

When the inner diameter r1 of the first layer 510 exceeds about 20% of the inner diameter r2 of the second layer 520, the frequency of the ultrasonic waves generated from the piezoelectric member 500 is increased. That is, ultrasonic waves having frequencies that are not suitable for cosmetic purposes may be generated from the ultrasound mask.

In addition, the inner diameter r2 of the second layer 520 may have a size of about 50% to about 70% of the outer diameter R2 of the second layer 520.

That is, the inner diameter r2 of the second layer 520 may be smaller than the outer diameter R2 of the second layer 520.

When the inner diameter r2 of the second layer 520 is less than 50% of the outer diameter R2 of the second layer 520, or the inner diameter r2 of the second layer 520 exceeds 70% of the outer diameter R2 of the second layer 520, the frequency of the ultrasonic waves generated from the piezoelectric member 500 is increased. That is, ultrasonic waves having frequencies that are not suitable for cosmetic purposes may be generated from the ultrasound mask, and the number of frequencies oscillating in the flexion mode may be less than three.

Table 1 below is for describing a frequency band generated when the outer and inner diameters of the first layer 510 and the outer and inner diameters of the second layer 520 are controlled within the above ranges.

TABLE 1

| First layer thickness: 300 μm | | | | Resonant frequency (khz) | | |
|---|---|---|---|---|---|---|
| Second layer thickness: 700 μm | | | | | Flexion | |
| First layer outer diameter (mm) | First layer inner diameter (mm) | Second layer outer diameter (mm) | Second layer inner diameter (mm) | Flexion mode resonance 1 | mode resonance 2 (Center frequency) | Flexion mode resonance 3 |
| 6 | 0 | 6 | 4 | 115 | 232 | 357 |
| 6 | 0 | 5.7 | 2.5 | 264 | 380 | 501 |
| 5 | 0 | 4.8 | 3 | 210 | 338 | 446 |
| 5 | 0.4 | 4.8 | 2.4 | 189 | 335 | 437 |
| 5 | 0.1 | 4.8 | 3 | 215 | 337 | 445 |
| 5 | 0 | 5 | 2.5 | 263 | 392 | 535 |
| 5 | 0 | 4.8 | 2.3 | 317 | 458 | 535 |

Referring to Table 1, it can be seen that the ultrasound mask according to the embodiment may implement multiple resonance of the flexion mode by controlling a thickness, an outer diameter, and an inner diameter of the first layer and a thickness, an outer diameter, and an inner diameter of the second layer to a specific numerical range.

That is, the ultrasound mask according to the embodiment may have at least two frequencies having a frequency within 150 before and after the center frequency while having the flexion mode.

Hereinafter, a manufacturing process of the ultrasound mask according to the first to third embodiments will be described with reference to FIGS. 27 to 30.

First, the first substrate 110 and the second substrate 120 are prepared, and the first wiring 210 and the second wiring 220 are formed on the first substrate 110 and the second substrate 120, respectively.

Referring to FIG. 27A, a copper pattern layer serving as a material of a wiring 200 may be formed on a substrate 100. As described above, the copper pattern layer may extend in the first direction, extend in the second direction, or extend in the first direction and the second direction.

Subsequently, referring to FIG. 27B, the same material as a material of the substrate may be applied on the substrate 100. In detail, the material of the substrate may be applied as much as a thickness of the wiring 200 disposed on the substrate 100.

Accordingly, the wiring 200 may be disposed on an engraved portion of the substrate 100, and the embossed portion E may be formed between the engraved portions on which the wiring 200 is disposed.

Finally, the first wiring 210 may be formed in a shape impregnated inside the first substrate 100, and the second wiring 220 may be formed in a shape impregnated inside the second substrate 120.

Subsequently, referring to FIG. 28, the piezoelectric member 500 may be disposed above the first substrate 110. The first electrode 410 and the second electrode 420 may be disposed on the lower surface and the upper surface of the piezoelectric member 500, respectively.

Then, the first adhesive layer 310 including a conductive material is disposed between the first electrode 410 and the first wiring 210, and the first electrode 410 and the first wiring 210 may be adhered to each other through the first adhesive layer 310 to dispose the piezoelectric member 500 on the first substrate 110.

Subsequently, referring to FIG. 29, the second substrate 120 on which the second wiring manufactured previously is formed may be disposed on the first substrate 110.

Then, the second adhesive layer 320 including a conductive material is disposed between the second electrode 420 and the second wiring 220, and the second electrode 420 and the second wiring 220 may be adhered to each other through the second adhesive layer 320 to dispose the piezoelectric member 500 on the lower surface of the second substrate 120.

That is, the first substrate 110, the second substrate 120, and the piezoelectric member 500 may be adhered and electrically connected through the first adhesive layer 310 and the second adhesive layer 320.

Subsequently, referring to FIG. 30, the protective layer 150 may be formed in a space between the piezoelectric members 500, that is, in a space between the piezoelectric members 500 between the first substrate 110 and the second substrate 120.

The protective layer 150 may include the same material as the first substrate 110 and the second substrate 120, and the first substrate 110, the second substrate 120, and the protective layer 150 may be integrated.

Alternatively, the protective layer 150 may include a material different from those of the first substrate 110 and the second substrate 120. For example, the first substrate 110 and the second substrate 120 may include a material that is relatively resistant to stress compared to the protective layer 150.

Subsequently, the first base layer 610, that is, a backing layer, may be disposed on the lower surface of the first substrate 110, and the second base layer 620, that is, a matching layer, may be disposed on the upper surface of the second substrate 120.

The first base layer 610 and the second base layer 620 may include the same material as the first substrate 110 and the second substrate 120, and the first substrate 110, the second substrate 120, and the protective layer 150 may be integrated.

Alternatively, the first base layer 610 and the second base layer 620 may include a material different from those of the first substrate 110 and the second substrate 120. For example, the first base layer 610 and the second base layer 620 may include a material that is relatively resistant to stress compared to the first substrate 110 and the second substrate 120.

The ultrasound mask according to the first to third embodiments may be manufactured by the same process as described above.

Hereinafter, a manufacturing process of the ultrasound mask according to the fourth to sixth embodiments will be described with reference to FIGS. 31 to 35.

Since a process according to FIGS. 31 to 34 is the same as the process according to FIGS. 27 to 30 described above, the following description will be omitted.

Referring to FIG. 35, the first metal layer 711 and the first cover layer 721 may be sequentially formed on the lower surface of the first base layer 610.

In addition, the second metal layer 712 and the second cover layer 722 may be sequentially formed on the upper surface of the second base layer 620.

The metal layers may include copper or the like, and the type of metal is not limited.

In addition, the cover layers may include a material the same as or similar to that of at least one of the substrate, the protective layer, and the base layers.

The ultrasound mask according to the fourth to sixth embodiments may be manufactured by the same process as described above.

Hereinafter, an overlapping relationship between the adhesive layer and the electrode of the ultrasound mask according to the embodiment will be described with reference to FIGS. 36 and 37.

Referring to FIGS. 36 and 37, the first adhesive layer 310 and the second adhesive layer 320 are disposed in a region overlapping one surface of the first electrode 410 and the second electrode 420.

The one surface of the first electrode 410 and the second electrode 420 may be greater than or equal to one surface of the first adhesive layer 310 and the second adhesive layer 320. That is, a contact area between the electrode and the adhesive layer may be smaller than that of one surface of the electrode.

When a region where one surface of the first adhesive layer 310 and the first electrode 410 overlap is defined as a first overlapping region, and a region where the second adhesive layer 320 and the other surface of the second electrode 420 overlap is defined as a second overlapping region, an overlapping area of the first overlapping region and the second overlapping region may be about 20% or more of the entire area of the first electrode 410 or the second electrode 420.

In detail, the overlapping area of the first overlapping region and the second overlapping region may be about 20% to about 100% of the entire area of the first electrode 410 or the second electrode 420.

When the overlapping area of the first overlapping region and the second overlapping region is less than about 20% of the entire area of the first electrode 410 or the second electrode 420, electrical characteristics of the wiring connected to the first electrode 410 or the second electrode 420 may be deteriorated, and thus reliability of the ultrasound mask may be deteriorated.

That is, the first adhesive layer 310 and the first electrode 410 and the second adhesive layer 320 and the second electrode 420 may completely overlap and be adhered to each other, or the first adhesive layer 310 and the second adhesive layer 320 may be in contact with each other while exposing one surface of the first electrode 410 or the second electrode 420.

In addition, overlapping areas of the first overlapping region and the second overlapping region of the adhesive layer disposed on a plurality of electrodes may have a uniform size.

For example, a difference between the overlapping areas of the first overlapping region and the second overlapping region of the adhesive layer disposed on the plurality of electrodes may be about 10% or less. In detail, the difference between the overlapping areas of the first overlapping region and the second overlapping region of the adhesive layer disposed on the plurality of electrodes may be 5% to 10%.

Accordingly, the ultrasonic waves generated from the plurality of piezoelectric members 500 may be transmitted in a uniform size to each area of the ultrasound mask by minimizing the difference between the overlapping areas of the first overlapping region and the second overlapping region.

Hereinafter, an ultrasound mask according to another embodiment will be described with reference to FIG. 38.

Referring to FIG. 38, the ultrasound mask according to another embodiment may include an indicator. In detail, an indicator 800 capable of identifying an operating state of the ultrasound mask may be disposed in one region of the ultrasound mask.

The indicator 800 may be disposed on an outer surface of the ultrasound mask so that the user may identify the indicator from the outside. That is, the ultrasound mask may be formed on a surface opposite to a surface on which substances such as cosmetics, and the like are disposed.

The indicator 800 may display various operating states of the ultrasound mask. For example, the indicator 800 may display the start/end of the ultrasound mask. Further, the indicator 800 may display a frequency band generated by the ultrasound mask.

The indicator 800 may include at least one of members capable of transmitting information to a user visually or aurally such as an LED, a display, and a buzzer.

The indicator 800 may be disposed outside the ultrasound mask 1000 to display an operation state of the ultrasound mask 1000. As an example, the indicator 800 may provide information on the start of the operation of the ultrasound mask 1000, information indicating that the operation is in progress, and information on the completion of the operation through auditory information generated from a buzzer. In addition, the indicator 800 may display the operation state according to the emission color of the LED. In addition, the indicator may display information on an operating frequency region through the display.

In addition, the indicator 800 may provide information on whether the ultrasound mask 1000 is closely adhered to the skin.

Hereinafter, an ultrasound mask according to still another embodiment will be described with reference to FIGS. 39 to 43.

Referring to FIGS. 39 to 43, the ultrasound mask according to still another embodiment may include a plurality of spacers 900 disposed on the base layer.

In detail, the ultrasound mask according to the embodiment may include the plurality of spacers 900 disposed on the second base layer 620 close to the skin, that is, the matching layer.

The plurality of spacers 900 may be disposed to be spaced apart from each other. For example, each of the spacers 900 may be disposed so as not to overlap a region where the piezoelectric member 500 is disposed. In detail, each of the spacers 900 may be disposed so as not to overlap the region where the piezoelectric member 500 is disposed so as not to affect the movement of the piezoelectric member to which the ultrasonic waves generated from the piezoelectric member 500 are transmitted. That is, the spacers 900 may be respectively disposed between the piezoelectric members 500.

The spacer 900 may be disposed on the matching layer to which a cosmetic ingredient 950 including cosmetics or drug substances applied to the skin of the human body is applied to prevent the cosmetic substances or drug substances from being aggregated in one region.

In detail, referring to FIG. 40, when the ultrasound mask is in contact with a material such as cosmetics applied to the skin, the material such as cosmetics moves outward form the region where the piezoelectric member is disposed by vibration and pressure generated from the piezoelectric member, so that a step may be formed.

Accordingly, an amount of the cosmetic substance is reduced in the region where the piezoelectric member is disposed, and thus the efficiency of movement of the cosmetic substance through ultrasonic waves may be deteriorated.

Accordingly, as shown in FIG. 41, by disposing the plurality of spacers 900 between regions in which the piezoelectric member is disposed, the cosmetic substances, and the like are moved to the outside when the ultrasound mask is in contact with the skin, and thus it is possible to prevent the amount of the cosmetic substances, and the like from being reduced in a region overlapping the piezoelectric member.

Referring to FIGS. 42 and 43, the spacers 900 may be disposed to be spaced apart in a dot shape between the piezoelectric members 500 as shown in FIG. 38 or may be formed in a linear shape connected to each other between the piezoelectric members 500 as shown in FIG. 39.

In the ultrasound mask according to still another embodiment, a plurality of spacers spaced apart from each other are disposed in a region not overlapping the piezoelectric member, and the ultrasound mask is in contact with the skin, and then it is possible to prevent the cosmetic material from being aggregated into one region by vibration and pressure generated from the piezoelectric member.

Therefore, it is possible to improve the efficiency of transmitting cosmetic substances of the ultrasound mask according to still another embodiment.

Hereinafter, an example of using the ultrasound mask according to the embodiment will be described with reference to FIGS. 44 and 45.

FIG. 44 is a view illustrating a user wearing a mask according to an embodiment, and FIG. 45 is a view illustrating a skin care device to which the mask according to the embodiment is applied.

Referring to FIG. 44, the user may wear the ultrasound mask 1000. The ultrasound mask 1000 may include the above-described opening 1010, and the user may secure a view through the opening 1010. In addition, the mask 1000 may include the above-described cutout portion 1020, and the ultrasound mask 1000 may be effectively close-adhered to the curved skin by the cutout portion 1020. In this case, one surface of the second base layer 620 may be in direct contact with the user's skin.

The ultrasound mask 1000 may be operated by receiving power through an external power connected to the ultrasound mask 1000. In addition, the ultrasound mask 1000 may be operated by receiving power through a power supply unit (not shown) disposed outside the ultrasound mask 1000, for example, on a lower surface of the second base layer 620.

In addition, referring to FIG. 45, the mask 1000 may be applied to a skin care device 1 to operate. In detail, referring to FIG. 41, the skin care device 1 may include a main body 10 in which one side thereof is open and including an accommodation space 11 therein.

The main body 10 may include a material that may be light and prevent damage from external impact or contact. As an example, the main body 10 may include a plastic or ceramic material, may have improved reliability from an external environment, and may protect the mask 1000 disposed inside the accommodation space 11. In addition, the main body 10 may include a viewing part 13 formed at a position corresponding to the user's eyes. The viewing part 13 may be formed in a region corresponding to the opening 1010 of the mask 1000, and the user may secure an external view through the viewing part 13.

The ultrasound mask 1000 may be disposed in the accommodation space 11 of the main body 10. The ultrasound mask 1000 may be disposed between the main body 10 and the user's skin. In detail, the first base layer 610 of the ultrasound mask 1000 may be disposed to face the accommodation space 11 of the main body 10, and the second base layer 620 of the ultrasound mask 1000 may be disposed to face the user's skin.

The ultrasound mask 1000 may be coupled to the main body 10. For example, the ultrasound mask 1000 may be fixed to a set position in the accommodation space 11 by a fastening member (not shown) and may have a structure that is detachable from the main body 10.

The ultrasound mask 1000 may receive power through the power supply unit (not shown) disposed outside the mask 1000. Alternatively, the ultrasound mask 1000 may be connected to the main body 10 to receive power through the power supply unit (not shown) disposed on the main body 10.

The ultrasound mask 1000 may further include a buffer member (not shown) disposed on the lower surface of the first base layer 610. The buffer member may be in direct contact with the first base layer 610 and may be disposed facing the accommodation space 11 of the main body 10. That is, a deformable member may be disposed between the main body 10 and the first base layer 610 of the mask 1000.

The deformable member may include a material of which shape is changed by external pressure. For example, the deformable member may include a material such as an air gap or a sponge, but the embodiment is not limited thereto, and may include various materials of which shape is changed by external pressure. Accordingly, when the user puts on the skin care device 1, the deformable member may be deformed into a shape corresponding to the shape of the user's face. Therefore, the ultrasound mask 1000 and the user's skin may be effectively close-adhered to each other.

In addition, when a plurality of users put on the skin care device 1, the deformable member is deformed to correspond to each face shape, so that the user's skin and the mask 1000 may be effectively close-adhered to each other.

The characteristics, structures, effects, and the like described in the above-described embodiments are included in at least one embodiment of the present invention, but are not limited to only one embodiment. Furthermore, the characteristic, structure, and effect illustrated in each embodiment may be combined or modified for other embodiments by a person skilled in the art. Thus, it should be construed that the contents related to such combination and modification are included in the scope of the present invention.

In addition, the above description has been focused on the embodiments, but it is merely illustrative and does not limit the present invention. Those skilled in the art to which the embodiments pertain may appreciate that various modifications and applications not illustrated above are possible without departing from the essential features of the embodiment. For example, each component particularly represented in the embodiments may be modified and realized. In addition, it should be construed that differences related to such a modification and an application are included in the scope of the present invention defined in the appended claims.

The invention claimed is:

1. An ultrasound mask comprising:
a first substrate;
a first wiring disposed inside the first substrate;
a second substrate disposed above the first substrate;
a second wiring disposed inside the second substrate;
a plurality of piezoelectric members disposed between the first substrate and the second substrate;
a first electrode connected to the first wiring and disposed on a lower surface of the piezoelectric member;
a second electrode connected to the second wiring and disposed on an upper surface of the piezoelectric member; and
a protective layer disposed between the first substrate, the second substrate, and the piezoelectric member,
wherein the first wiring is arranged in a first direction,
the second wiring is arranged in a second direction different from the first direction,
the first wiring and the second wiring each include a plurality of interconnection wirings disposed between the piezoelectric members, and
the interconnection wiring is in contact with the protective layer.

2. The ultrasound mask of claim 1, wherein the first wiring and the second wiring are arranged in a direction in which the first direction and the second direction intersect each other.

3. The ultrasound mask of claim 1, wherein the first wiring and the second wiring have a curvature of 5R to 15R.

4. The ultrasound mask of claim 1, further comprising:
a first base layer disposed under the first substrate; and
a second base layer disposed above the second substrate.

5. The ultrasound mask of claim 4, wherein the first base layer reflects ultrasonic waves of a direction of the first substrate to a direction of the second substrate, and
the second base layer includes an acoustic matching layer.

6. The ultrasound mask of claim 4, wherein the ultrasonic waves move in the direction from the first substrate to the second substrate.

7. The ultrasound mask of claim 4, wherein a thickness of the first base layer is smaller than a thickness of the second base layer.

8. The ultrasound mask of claim 4, further comprising
a first metal layer disposed under the first base layer;
a first cover layer disposed under the first metal layer;
a second metal layer disposed above the second base layer; and
a second cover layer disposed above the second metal layer.

9. A skin care device comprising:
a body having an open side and having an accommodation space inside the open region; and
a mask disposed in the open region and connected to the body,
wherein the mask includes a mask according to claim 1.

10. An ultrasound mask comprising:
a first substrate;
a first wiring disposed inside the first substrate;
a second substrate disposed above the first substrate;
a second wiring disposed inside the second substrate;
a plurality of piezoelectric members disposed between the first substrate and the second substrate;
a first electrode connected to the first wiring and disposed on a lower surface of the piezoelectric member;
a second electrode connected to the second wiring and disposed on an upper surface of the piezoelectric member; and
a protective layer disposed between the first substrate, the second substrate, and the piezoelectric member,
wherein the first wiring is arranged in a first direction,
the second wiring is arranged in a second direction different from the first direction, and
the piezoelectric member generates ultrasonic waves having at least three frequencies oscillating in a flexion mode.

11. The ultrasound mask of claim 10, wherein the piezoelectric member generates ultrasonic waves having at least two frequencies oscillating in the flexion mode at 150 kHz before and after a center frequency of the ultrasonic waves oscillating in the flexion mode.

12. The ultrasound mask of claim 11, wherein the center frequency of the ultrasonic waves is 200 kHz to 400 kHz.

13. An ultrasound mask comprising:
a first substrate;
a first wiring disposed inside the first substrate;
a second substrate disposed above the first substrate;
a second wiring disposed inside the second substrate;
a plurality of piezoelectric members disposed between the first substrate and the second substrate;
a first electrode connected to the first wiring and disposed on a lower surface of the piezoelectric member;
a second electrode connected to the second wiring and disposed on an upper surface of the piezoelectric member; and
a protective layer disposed between the first substrate, the second substrate, and the piezoelectric member,
wherein the first wiring is arranged in a first direction,
the second wiring is arranged in a second direction different from the first direction,
the piezoelectric member includes a first layer in contact with the second electrode and a second layer that is disposed under the first layer and in contact with the first electrode,
the first layer includes a metal and the second layer includes a piezoelectric material, and
a through-hole is formed in at least one of the first layer and the second layer.

14. The ultrasound mask of claim 13, wherein the first layer includes a metal, and
the second layer includes a piezoelectric material.

15. The ultrasound mask of claim 13, wherein a thickness of the first layer and a thickness of the second layer are 200 μm to 1500 μm, and
the thickness of the first layer has a thickness of 80% to 120% of the thickness of the second layer.

16. The ultrasound mask of claim 15, wherein an outer diameter of the first layer and an outer diameter of the second layer are about 3 mm to 8 mm, and
the outer diameter of the first layer has a size of 92% to 108% of the outer diameter of the second layer.

17. The ultrasound mask of claim 16, wherein an inner diameter of the first layer is 0 mm to 1.5 mm and an inner diameter of the second layer is 1.5 mm to 5.6 mm, and
the inner diameter of the first layer has a size of 20% or less of the inner diameter of the second layer.

18. The ultrasound mask of claim 17, wherein the inner diameter of the second layer has a size of 50% to 70% of the outer diameter of the second layer.

19. The ultrasound mask of claim 13, wherein the piezoelectric member generates ultrasonic waves in a direction from the first substrate to the second substrate, and
the piezoelectric member generates ultrasonic waves having at least three frequencies oscillating in a flexion mode.

20. The ultrasound mask of claim 19, wherein the piezoelectric member generates ultrasonic waves having at least two frequencies oscillating in the flexion mode at 150 kHz before and after a center frequency of the ultrasonic waves oscillating in the flexion mode, and
the center frequency of the ultrasonic waves is 200 kHz to 400 kHz.

\* \* \* \* \*